US006599498B1

(12) United States Patent
Groman et al.

(10) Patent No.: US 6,599,498 B1
(45) Date of Patent: Jul. 29, 2003

(54) HEAT STABLE COLLOIDAL IRON OXIDES COATED WITH REDUCED CARBOHYDRATES AND CARBOHDRATE DERIVATIVES

(75) Inventors: Ernest V. Groman, Brookline, MA (US); Kenneth G. Paul, Holliston, MA (US); Timothy B. Frigo, Waltham, MA (US); Howard Bengele, Canton, MA (US); Jerome M. Lewis, Newton, MA (US)

(73) Assignee: Advanced Magnetics, Inc., Cambridge, MA (US)

( * ) Notice: Subject to any disclaimer, the term of this patent is extended or adjusted under 35 U.S.C. 154(b) by 0 days.

(21) Appl. No.: 09/521,264

(22) Filed: Mar. 8, 2000

Related U.S. Application Data

(60) Provisional application No. 60/128,579, filed on Apr. 9, 1999.

(51) Int. Cl.$^7$ ................... A61B 5/055; A61K 9/16; A61K 9/50; A61K 31/70; A61K 31/715; A01N 43/04

(52) U.S. Cl. ................ 424/9.34; 424/9.35; 424/493; 514/54; 514/59

(58) Field of Search ................ 424/9.3, 9.32, 424/9.35, 493; 514/54, 59

(56) References Cited

U.S. PATENT DOCUMENTS

| | | | | |
|---|---|---|---|---|
| 4,770,183 A | | 9/1988 | Groman et al. ......... 128/654 |
| 4,827,945 A | | 5/1989 | Groman et al. ......... 128/653 |
| 5,055,288 A | | 10/1991 | Lewis et al. ............ 424/9 |
| 5,102,652 A | | 4/1992 | Groman et al. ........... 424/9 |
| 5,128,121 A | * | 7/1992 | Berg et al. ............... 424/9 |
| 5,160,726 A | | 11/1992 | Josephson et al. ........ 424/9 |
| 5,204,457 A | | 4/1993 | Maruno et al. ......... 536/101 |
| 5,262,176 A | | 11/1993 | Palmacci et al. .......... 424/9 |
| 5,985,245 A | * | 11/1999 | Golman et al. ......... 424/9.36 |
| 6,165,378 A | | 12/2000 | Maruno et al. ......... 252/62.53 |

FOREIGN PATENT DOCUMENTS

| | | | |
|---|---|---|---|
| EP | 0 230 768 B1 | 12/1986 | ......... B03C/1/00 |
| EP | 0 450 092 | 10/1991 | ......... C08B/11/12 |
| WO | WO 91 09678 | 7/1991 | ......... G01N/33/543 |
| WO | WO 96 09840 | 4/1996 | ......... A61K/49/00 |
| WO | WO 00 30657 | 6/2000 | ......... A61K/31/715 |

OTHER PUBLICATIONS

Grimm, Jan et al. "Characterization of Ultrasmall, Paramagnetic Magnetite Particles as Superparamagnetic Contrast Agents in MRI", Database Chemabs [Online]: *Invest. Radiol.*, 2000, vol. 35(9), pp. 553–556.
Voorhees, A.B. et al., *Proc. Soc. Exp. Biol. Med.* 1951, 76:254.
Squire, J.R. et al., in "Dextran, Its Properties and Use in Medicine" Charles C Thomas, Springfield, IL, 1955.
Hanna, C.H. et al., *Am. J. Physiol.* 1957, 191:615.
Briseid, G. et al., *Acta Pharmcol. Et toxical.*, 1980, 47:119–126.
Kitchen, R., *Proc. Sugar Process. Res. Conf.*, 1983, 232–47.
Jue, C. K. et al., *J. Biochem. Biophys. Methods*, 1985, 11:109–15.
Hedin, H. et al., *Int. Arch. Allergy and Immunol.*, 1997:113:358–359.
Kumar K., *J. Liq. Chromatogr. Relat. Tehcnol.*, 1997, 20, 3351–3364.
Hasegawa et al. *Japan J. Appl. Phys.*, 1998, Part I:37(3A):1029.

\* cited by examiner

*Primary Examiner*—Sreeni Padmanabhan
(74) *Attorney, Agent, or Firm*—Bromberg & Sunstein LLP

(57) ABSTRACT

Compositions, methods of making the compositions, and methods of using the compositions are provided for an enhanced magnetic resonance imaging agent and a hematinic agent, the agents comprising carboxyalkylated reduced polysaccharides coated ultrasmall superparamagnetic iron oxides. Methods of use of the carboxymethyl reduced dextran as a plasma extender are provided.

26 Claims, 12 Drawing Sheets

HEAT STABLE COLLOIDAL IRON OXIDES COATED WITH REDUCED CARBOXYHYDRATES AND CARBOHDRATE DERIVATIVES

RELATED APPLICATIONS

This application claims the benefit of Provisional Application No. 60/128,579, filed in the United States Patent and Trademark Office on Apr. 9, 1999, and which is hereby incorporated by reference herein.

TECHNICAL FIELD

The field relates to compositions which are carboxymethyl reduced polysaccharides, and methods for use as plasma extenders and for coating iron oxide particles, and compositions comprised of superparamagnetic and non-superparamagnetic iron oxides coated with a reduced polysaccharide or derivatized reduced polysaccharide, and methods for use as MRI contrast agents and hematinics.

BACKGROUND

Since the invention of magnetic resonance imaging (MRI), a parallel technology of injectable chemicals called contrast agents has developed. Contrast agents play an important role in the practice of medicine in that they help produce more useful MRI images for diagnostic purposes. In particular, two classes of imaging agents have been developed and adopted in clinical practice. These are: low molecular weight gadolinium complexes such as Magnavist®; and colloidal iron oxides. Neither of these two types of agents is ideal. Problems encountered with these agents are shown in Table 1, and include: expense of components; inefficiency of synthesis; loss of coating if sterilized by autoclaving; narrow range of organ uptake for purposes of imaging; side-effects; restriction of use to either first pass or equilibrium dosing; and others that are described herein. Agents that overcome these problems, and that combine the properties of these two types of contrast agents, are highly desirable.

TABLE 1

Comparison of ideal properties of MRI contrast agents with properties of low molecular weight gadolinium based contrast agents and colloidal iron oxides.

| Properties of an ideal contrast agent | low molecular weight gadolinium | colloidal iron oxides |
| --- | --- | --- |
| Low production costs: efficient synthesis | Yes | No |
| Autoclavable without excipients | Yes | No |
| T1 agent | Yes | Sometimes |
| T2 agent | No | Yes |
| Non toxic at vast excess | Yes | No |
| Imaging vascular compartment at early phase (as a bolus administration) and at a late stage (equilibrium phase) | No | No |
| Multiple administration in single examination | No | No |
| Image of multiple target organs | Yes | Sometimes |
| Bolus injection | Yes | No |
| Low volume of injection | No | No |
| Iron source for anemia | No | Yes |

SUMMARY

An embodiment of the invention is a method of providing an iron oxide complex for administration to a mammal subject, the method comprising: producing a reduced polysaccharide iron oxide complex, and sterilizing the complex by autoclaving. In general, the reduced polysaccharide is a reduced polymer of glucose. An example of a reduced polymer of glucose is a reduced dextran. The reduced polysaccharide is produced through reaction of a polysaccharide with a reagent selected from the group consisting of a borohydride salt or hydrogen in the presence of a hydrogenation catalyst. In a further aspect of the method, the iron oxide is superparamagnetic.

Another preferred embodiment of the invention is a method of providing an iron oxide complex for administration to a mammalian subject, the method comprising: producing a derivatized reduced polysaccharide iron oxide complex, and sterilizing the complex by autoclaving. According to this method, producing the complex can include derivatizing a reduced polysaccharide by caboxyalkylation, for example, wherein the carboxyalkylation is a carboxymethylation. The term "derivatizing" and related terms (e.g. derivatives, derivatized, derivatization, etc) refer to the conventional sense of functionalization at the reactive sites of the composition. Further according to this method, the reduced polysaccharide can be a reduced dextran. The derivatized, reduced polysaccharide can be isolated as the sodium salt and does not contain an infrared absorption peak in the region of 1650–1800 $cm^{-1}$. In one aspect of the method, producing the derivatized reduced polysaccharide is achieved at a temperature of less than approximately 50° C. In another aspect of the method, producing the derivatized reduced polysaccharide is achieved at a temperature of less than approximately 40° C. In a further aspect of the method, the iron oxide is superparamagnetic.

In yet another embodiment, the invention provides a method of formulating an iron oxide complex coated with a reduced polysaccharide. This composition is for pharmacological use and the composition has decreased toxicity in comparison to an analogous iron oxide complex coated with native polysaccharide. The method of formulating such an iron oxide complex comprises: producing a reduced polysaccharide iron oxide complex, and sterilizing the complex by autoclaving. The formulation provides polysaccharide which was produced by reacting the polysaccharide with one of a reducing agent selected from the group consisting of a borohydride salt or hydrogen in the presence of an hydrogenation catalyst. The reduced polysaccharide iron oxide complex has such decreased toxicity. In a further aspect of the method, the iron oxide is superparamagnetic.

In yet another embodiment, the invention provides a method of formulating an iron oxide complex coated with a reduced derivatized polysaccharide. This composition is for pharmacological use and the composition has decreased toxicity in comparison to an analogous iron oxide complex coated with native derivatized polysaccharide. The method of formulating such an iron oxide complex comprises: producing a reduced derivatized polysaccharide iron oxide complex; and sterilizing the complex by autoclaving. According to this method, producing the complex can include derivatizing a reduced polysaccharide by carboxyalkylation, for example, wherein the carboxyalkylation is a carboxymethylation. Further according to this method, the reduced polysaccharide can be a reduced dextran. The derivatized, reduced polysaccharide can be isolated as the sodium salt and does not contain an infrared absorption peak in the region of 1650–1800 $cm^{-1}$. In one aspect of the method, producing the derivatized reduced polysaccharide is achieved at a temperature of less than approximately 50° C. In another aspect of the method, producing the derivatized reduced polysaccharide is achieved at a temperature of less than approximately 40° C. In a further aspect of the method, the iron oxide is superparamagnetic.

Another embodiment of the invention provides a reduced derivatized polysaccharide iron oxide complex with T1 and T2 relaxation properties to allow contrast agent signal enhancement with T1 sequences and signal diminishment with T2 sequences. A further aspect of the embodiment is that the reduced derivatized polysaccharide iron oxide can be administered multiple times for sequential imaging in a single examination. Yet another aspect of the agent is that it can be used to image multiple organ systems including the vascular system, liver, spleen, bone marrow, and lymph nodes.

Another embodiment of the invention provides a reduced polysaccharide iron oxide complex for use as an intravenous iron supplement.

Another embodiment of the invention provides a reduced derivatized polysaccharide iron oxide complex for use as an intravenous iron supplement.

In yet a further embodiment, the invention provides an improved method of administering to a mammalian subject an autoclaved reduced polysaccharide iron oxide complex. The improved method of administration comprising: injection of an autoclaved reduced polysaccharide iron oxide complex in a volume of 15 ml or less. In another aspect of the embodiment the injected volume is injected as a bolus. In a further aspect of the method, the iron oxide is superparamagnetic. In a further aspect of the embodiment the injected volume provides improved image quality.

In yet a further embodiment, the invention provides an improved method of administering to a mammalian subject an autoclaved derivatized reduced polysaccharide iron oxide complex. The improved method of administration comprising: injection of an autoclaved reduced derivatized polysaccharide iron oxide complex in a volume of 15 ml or less. In another aspect of the embodiment the injected volume is injected as a bolus. In a further aspect of the method, the iron oxide is superparamagnetic. In a further aspect of the embodiment the injected volume provides improved image quality.

An embodiment of the invention provides an improved method of administering to a mammalian subject a reduced polysaccharide iron complex in a manner that the composition provides reduced toxicity, wherein the improvement comprises utilizing a reduced polysaccharide in formulation of the composition. In a further aspect of the embodiment, the iron oxide is superparamagnetic.

An embodiment of the invention provides an improved method of administering to a mammalian subject a reduced derivatized polysaccharide iron complex in a manner that the composition provides reduced toxicity, wherein the improvement comprises utilizing a reduced derivatized polysaccharide in formulation of the composition. In a further aspect of the embodiment, the iron oxide is superparamagnetic.

An embodiment of the invention provides a reduced polysaccharide iron oxide complex, wherein the reduced polysaccharide is derivatized, for example, the reduced derivatized polysaccharide is a carboxyalkyl polysaccharide. The carboxyalkyl is selected from the group consisting of carboxymethyl, carboxyethyl and carboxypropyl. Further, the reduced polysaccharide can be a reduced dextran, for example, the reduced dextran can be a reduced carboxymethyl dextran. A further aspect of this embodiment of the invention is that the level of derivatization of the reduced dextran is at least 750 μmole but less than 1500 μmole of carboxyl groups per gram of polysaccharide wherein said composition has reduced toxicity relative to composition with respect to lower levels of derivatization.

An embodiment of the invention provides a reduced polysaccharide iron oxide complex, such complex being stable at a temperature of at least approximately 100° C. In a preferred embodiment, such complex is stable at a temperature of approximately 121° C. In an even more preferred aspect of the reduced polysaccharide iron oxide complex, such complex is stable at a temperature of at least 121° C. for a time sufficient to sterilize the complex. In a further aspect of the embodiment, the iron oxide is superparamagnetic.

An embodiment of the invention provides a reduced derivatized polysaccharide iron oxide complex, such complex being stable at a temperature of at least approximately 100° C. In a preferred embodiment, such complex is stable at a temperature of approximately 121° C. In an even more preferred aspect of the reduced polysaccharide iron oxide complex, such complex is stable at a temperature of at least 121° C. for a time sufficient to sterilize the complex. In a further aspect of the embodiment, the iron oxide is superparamagnetic.

A preferred embodiment of the invention is a method of formulating for pharmacological use a reduced polysaccharide iron oxide complex having increased pH stability in comparison to the corresponding native dextran iron oxide, the method comprising: providing dextran; and reacting the dextran with a borohydride salt or hydrogen in the presence of an hydrogenation catalyst, reacting the reduced dextran with iron salts to provide a formulation having a stable pH.

A preferred embodiment of the invention is a method of formulating for pharmacological use a reduced derivatized polysaccharide iron oxide complex having increased pH stability in comparison to the corresponding native dextran iron oxide, the method comprising: providing dextran; and reacting the dextran with a borohydride salt or hydrogen in the presence of an hydrogenation catalyst, reacting the reduced dextran with iron salts to provide a formulation having a stable pH.

In another embodiment, the invention provides a method of formulating a reduced derivatized dextran composition for pharmacological use wherein the composition has decreased toxicity in comparison to native dextran; comprising: producing a reduced derivatized polysaccharide; and sterilizing the product by autoclaving. According to this method, the reduced polysaccharide is obtained by reacting the native polysaccharide with one of several reducing agents selected from the group consisting of a borohydride salt, or hydrogen in the presence of a hydrogenation catalyst. In a preferred aspect of the embodiment the polysaccharide is dextran. Producing the composition can include derivatizing a reduced polysaccharide by carboxyalkylation, for example, wherein the carboxyalkylation is a carboxymethylation. Further according to this method, the reduced polysaccharide can be a reduced dextran. The derivatized, reduced polysaccharide can be isolated as the sodium salt and does not contain an infrared absorption peak in the region of 1650–1800 $cm^{-1}$. In one aspect of the method, producing the derivatized reduced polysaccharide is achieved at a temperature of less than approximately 50° C. In another aspect of the method, producing the derivatized reduced polysaccharide is achieved at a temperature of less than approximately 40° C.

An embodiment of the invention provides an improved method of administering to a mammalian subject a reduced derivatized polysaccharide in a manner that the composition provides reduced toxicity, wherein the improvement comprises utilizing a reduced polysaccharide in formulation of the composition.

An embodiment of the invention provides a reduced polysaccharide, wherein the reduced polysaccharide is derivatized, for example, the reduced derivatized polysaccharide is a carboxyalkyl polysaccharide. The carboxyalkyl is selected from the group consisting of carboxymethyl, carboxyethyl and carboxypropyl. Further, the reduced polysaccharide can be a reduced dextran. A further aspect of this embodiment of the invention is that the level of derivatization of the reduced dextran is at least 750 micromolar of carboxyl groups per gram of polysaccharide wherein said composition has reduced toxicity relative to composition with lower levels of derivatization.

Another embodiment of the invention is a method of formulating a dextran composition for pharmacological use and having decreased toxicity in comparison to native dextran, the method comprising: providing dextran; and reacting the provided dextran with a borohydride salt or hydrogen in the presence of an hydrogenation catalyst followed by carboxymethylation, the reduced carboxymethylated dextran having decreased toxicity.

Another embodiment of the invention is an improved method of administering to a mammalian subject a polysaccharide composition of the type wherein the composition includes dextran in a manner that the composition provides reduced toxicity, wherein the improvement comprises utilizing reduced carboxymethylated dextran in lieu of dextran in the formulation. In another aspect, an embodiment of the invention is an improved method of administering to a mammalian subject a polysaccharide in a manner that the composition provides reduced toxicity, wherein the improvement comprises utilizing a reduced carboxymethylated polysaccharide in formulation of the composition.

An embodiment of the invention provides a method of use of reduced derivatized dextrans as blood expanders.

DETAILED DESCRIPTION OF SPECIFIC EMBODIMENTS

Figure 1:
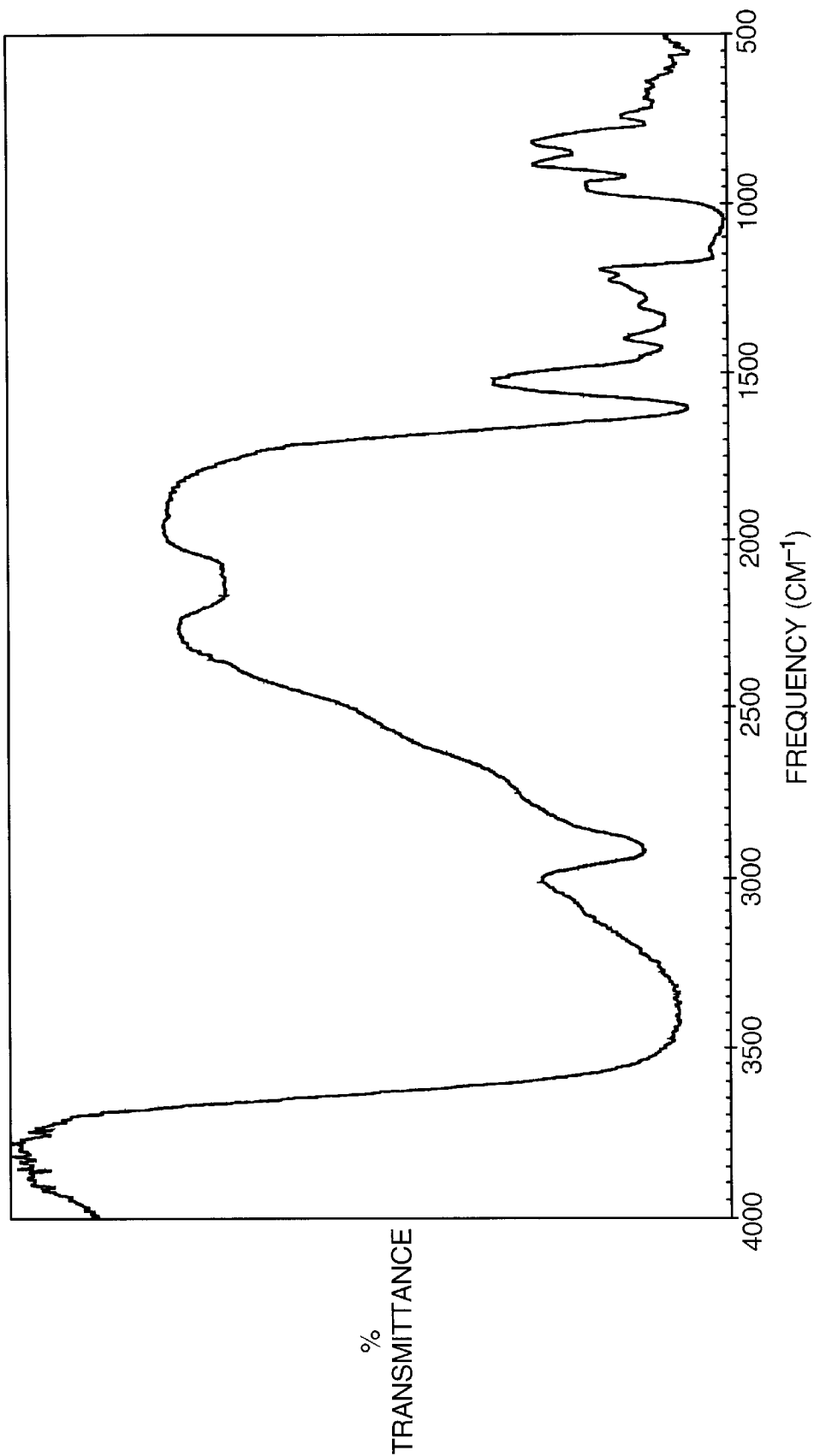
FIG. 1 shows a Fourier transform infrared (FTIR) spectrographic analysis of carboxymethyl reduced dextran (CMRD) sodium salt obtained with Example 5.
Figure 2:
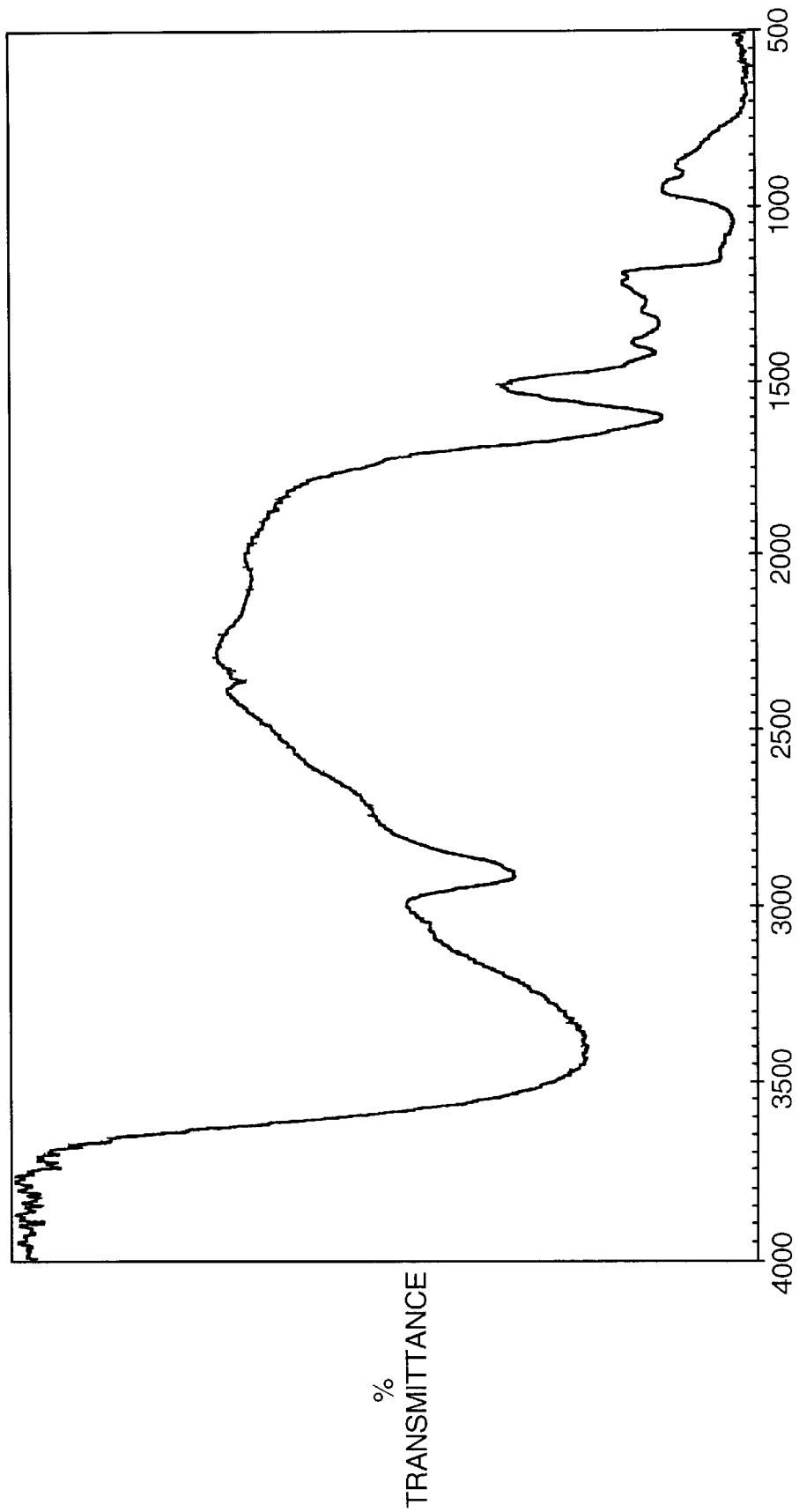
FIG. 2 shows an FTIR spectrographic analysis of sodium salt CMRD coated ultrasmall superparamagnetic iron oxide (USPIO; see U.S. Pat. No. 5,055,288) obtained in Example 31.

Table 1 summarizes the characteristics of two classes of MRI contrast agents that have been previously described, and shows a comparison of their characteristics to those of an ideal contrast agent. Agents of the invention embody the ideal characteristics, as shown herein.

Surprisingly, the development and synthesis of preparations of ultrasmall superparamagnetic iron oxide (USPIOs) coated with polysaccharide reduced dextrans and derivatives of reduced dextrans, such as the agents with the desirable properties as shown herein, are derived from a change in the chemical nature of one constituent, dextran T10. This change involved reduction of the terminal aldehyde group to an alcohol of the polysaccharide used in its synthesis to an alcohol (Scheme 1). Scheme 1 illustrates the chemical change in a polysaccharide such as dextran upon treatment with sodium borohydride. The hemiacetal form of the polysaccharide (structure 1) is in equilibrium with the aldehyde form of the polysaccharide (structure 2). Structure 2 represents less than 0.01% of the equilibrium mixture (Brucker, G. (1974) *Organic Chemistry: Amino Acids, Peptides and Carbohydrates.*, Tankonykiado Press, Budapest, p. 991). Treatment of structure 2 with sodium borohydride results in its irreversible conversion to the linear polyol form of the polysaccharide (structure 3). The dynamic equilibrium between structures 1 and 2 allows complete conversion, when treated with sodium borohydride, to the linear polyol (structure 3).

Scheme 1:

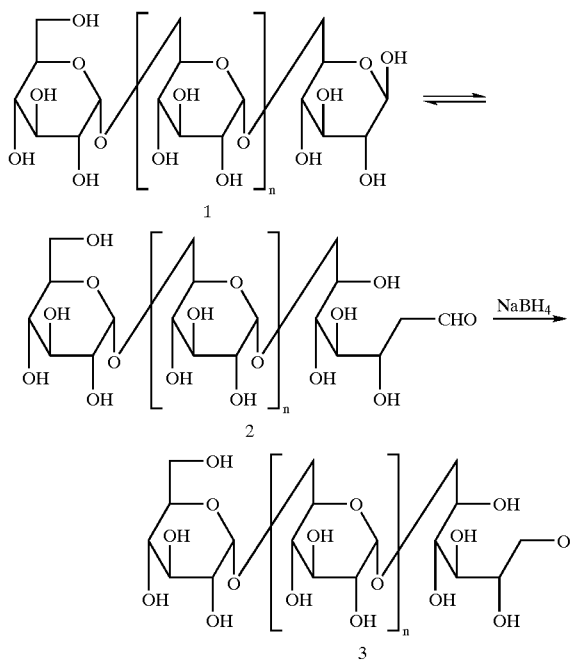

Dextran coated superparamagnetic iron oxide particles have particular interest as magnetic resonance imaging (MRI) contrast agents because of their ability to enhance images of the liver and lymph. Feridex I.V.® (Advanced Magnetics, Inc., Cambridge Mass.) is a dextran coated superparamagnetic iron oxide MRI contrast agent, and approved for use in humans. Combidex® (Advanced Magnetics, Inc.) is a dextran coated ultrasmall superparamagnetic iron oxide (USPIO) which has completed Phase III clinical trials for both liver imaging and Phase III trials for lymph imaging. Combidex® has a smaller mean diameter (20 nm) than Feridex I.V.® (60 nm), which gives it a different biodistribution in humans. Combidex® is made by addition of base to a solution of dextran, ferric chloride and ferrous chloride. The synthetic process comprises combining the ingredients, heating, and purifying by ultrafiltration. However, the yield of dextran added to the particles in the reaction is inefficient. Pharmaceutical grade dextran is the most expensive component of the Combidex® synthesis. A more efficient use of dextran in the synthesis of Combidex® is desirable to lower production costs.

Terminal sterilization (autoclaving) is a preferred method of sterilizing drugs for injection. However, many superparamagnetic iron oxide colloids that are used as MRI contrast agents are synthesized with polymer coatings and coverings that influence the biodistribution and elimination of these colloids. Upon exposure to the heat for the duration of the autoclaving process, the polymer coating can become dissociated from the iron oxide cores. The functional consequences of polymer dissociation from the iron oxide are physical changes in the material, such as clumping, biodistribution changes (changes in plasma half life), and changes in toxicity profile (potential increases in adverse events). For example, a substantial decrease in the pH of the solution can be detected following autoclaving of iron dextran particles, and the pH continues to fall upon further storage.

Several solutions to the problem of imparting resistance to heat stress have been described. Palmacci et al., U.S. Pat. No. 5,262,176, hereby incorporated herein by reference, used crosslinked dextran to stabilize the covering on the iron oxide particles prior to autoclaving. The crosslinking process uses noxious agents such as epichlorohydrin and epibromohydrin, which must be removed from the colloid after the crosslinking reaction.

Methods of preventing clumping of the colloid induced by heat stress that have no effect on coating dissociation have also been described. These methods generally include the use of excipients during the autoclaving process. Groman et al., U.S. Pat. No. 4,827,945, and Lewis et al., U.S. Pat. No. 5,055,288, both patents hereby incorporated herein by reference, use citrate to prevent clumping of the particles when the coating dissociates. Groman et al., U.S. Pat. No. 5,102,652, hereby incorporated herein by reference, uses low molecular weight carbohydrates such as mannitol to prevent clumping during autoclaving. These excipients increase the cost and complexity of manufacturing the product, yet do not solve the problem of dissociation of the polymer from the iron particle.

Josephson et al., U.S. Pat. No. 5,160,726, hereby incorporated herein by reference, avoids heat stress on the coating by using filter sterilization rather than heat to sterilize the colloid. Filter sterilization is expensive since both the sterilization process and container closure must be performed in a germ free environment. Additionally, filter sterilizing has a higher rate of failure than the process of autoclaving, which reflects the inability to obtain an environment for the filtration step that is entirely germ free.

Maruno et al., U.S. Pat. No. 5,204,457, describes a carboxymethyl-dextran coated particle with improved stability up to 80° C. for an extended period but does not teach use of terminal sterilization by autoclaving. Hasegawa et al. (Japan J. Appl. Phys., Part 1, 37(3A):1029–1032, 1998) describes carboxymethyl dextran coated iron particles with thermal stability at 80° C., but does not teach use of a carboxymethyl reduced dextran coated particle, nor of terminal sterilization by autoclaving.

Magnetic resonance imaging agents act by affecting the normal relaxation times, principally on the protons of water. There are two types of relaxation, one known as spin-spin or T1 relaxation, and the second known as spin-lattice or T2 relaxation. T1 relaxation generally results in a brightening of the image caused by an increase in signal. T1 processes are most useful in imaging of the vascular system. T2 relaxation generally results in a darkening of the image caused by a decrease in signal. T2 processes are most useful in imaging of organs such as the liver, spleen, or lymph nodes that contain lesions such as tumors. All contrast agents have both T1 and T2 properties; however, either T1 or T2 relaxation can characterize the dominant relaxation property of a particular contrast agent. Low molecular weight gadolinium based contrast agents are T1 agents, and have primary application in the imaging of vascular related medical problems such as stroke and aneurysms and the brain. Iron oxide based colloidal contrast agents are T2 agents, and have primary application in imaging tumors of the liver and lymph nodes (prostate and breast cancer). An agent possessing both T1 and T2 properties would be desirable. Using such an agent would (I) provide a single drug for all applications, and simplify the inventory of the pharmacy, (ii) simplify imaging in the MRI suite, and (iii) improve patient care by permitting simultaneous examination of multiple medical problems in a single patient during a single examination, rather than requiring use of either a T1 or a T2 contrast agent.

A dextran can elicit a sometimes fatal anaphylactic response when administered intravenously (i.v.) in man (Briseid, G. et al., *Acta Pharmcol. Et Toxicol.*, 1980, 47:119–126; Hedin, H. et al., *Int. Arch. Allergy and Immunol.*, 1997:113:358–359). Related adverse reactions have been observed also on administration of magnetic dextran coated iron oxide colloids. Non-magnetic dextran coated iron oxide colloids that have utility as hematinics, particularly as an adjunct to erythropoietin treatment for end stage renal dialysis patients, may have side effects.

Information regarding-anatomical features within the vascular system can be obtained using contrast agents in two ways. When the contrast agent is first administered as a bolus, it initially passes through the vascular tree as a relatively coherent mass. Coordinating the time of imaging of the desired anatomical feature to the time when the bolus passes through that feature can provide useful information. This technique of contrast agent use is called first pass imaging. At a later time, the bolus has been diluted by mixing, and attains an equilibrium concentration in the vascular system. Under certain circumstances, this equilibrium or steady state can offer useful information. Imaging can be performed at an early phase, within minutes after injection of the contrast agent ("first pass"), and at a later phase, from about ten minutes after injection of the contrast agent (equilibrium phase). Gadolinium agents are suited only for first pass imaging due to their ready diffusion from the vascular system into the interstitial spaces of the tissues. Previously described colloidal iron oxides are useful for the equilibrium due to their requirement for dilute administration over a prolonged time period. Colloidal iron oxides do not leak into the interstitial space but can remain in the vascular system for hours. An agent offering the opportunity to perform both first pass imaging and equilibrium imaging would be desirable.

During administration in a medical setting of a contrast agent for "first pass" imaging, the timing of imaging and passage of the "first pass" of the contrast agent may not coincide. If a useful image was not obtained, it becomes desirable to administer a second dose of contrast agent to obtain another "first pass" image. On other occasions radiologists find it useful to examine several volumes within the patient requiring a multiple dosing regimen of contrast agent in order to obtain "first pass" images at each of multiple sites of interest. With gadolinium contrast agents, this multiple administration "first pass" application is not possible because the gadolinium leaks out of the vascular space producing a fuzzy background around blood vessels of interest. Current iron oxide colloidal based contrast agents are not suitable as they are administered not as a bolus, but as a dilute solution over a long time, obviating "first pass" applications.

Diagnosis of tumor progression in cancer patients is important for characterizing the stage of the disease, and for assessing treatment. To minimize cost and discomfort to the patient, it is desirable in an MRI examination to administer a single dose of contrast agent that would allow assessment of multiple organ systems that might be affected by the disease. For instance, in primary breast cancer, it is desirable to assess tumor status in the breast and at multiple metastatic sites including the liver, spleen, bone marrow, and lymph nodes. Administration of gadolinium based contrast agents can not satisfy this requirement due to their short half life in the body, their leakage into the vascular system, and their inability to concentrate within organs of interest. Iron oxide colloid based contrast agents such as Combidex® can serve in this multiple capacity while Feridex I.V.®, another iron oxide colloid contrast agent, is limited to imaging the liver and the spleen.

Administration of a contrast agent in a small volume (less then 5 ml) is desirable, as small volume administration improves the resolution obtained from first pass imaging, and minimizes injection time and discomfort to the patient. Gadolinium based contrast agents are administered in volumes of about 30 ml due to constraints caused by the solubility and potency of these agents. Currently, iron oxide based contrast agents are administered as a dilute solution in a large volume (50–100 ml) over an extended period of time (30 minutes). These constraints arise from safety issues associated with the rapid and concentrated administration of iron oxide based agents. Bolus injection is desirable in that it allows first pass imaging and shortens contact time between the patient and health care provider. Further bolus injection allows the practitioner to administer the contrast agent while the subject is in the MRI apparatus during the examination, thereby optimizing efficient use of instrument imaging time. Gadolinium based agents can be administered as a bolus.

Gadolinium based contrast agents consist of a chelating molecule and the gadolinium cation. Gadolinium is a toxic element and must be excreted from the body to avoid toxicity. Colloidal iron oxides are not excreted from the body but are processed in the liver and other organs to metabolic iron, such as the iron in hemoglobin. Thus, compositions of the invention can serve as an iron supplement for patients suffering from anemia, and are especially useful for patients undergoing treatment with erythropoietin.

An embodiment of the invention provides a method for the synthesis of a colloid of an iron oxide associated with a water soluble polysaccharide coating in a manner that mitigates dissociation of the coating from the iron oxide when the material is subjected to heat stress.

As used herein and in the accompanying claims, "heat stress" is defined as heating the colloid to approximately 121° C. or higher for about 30 minutes at neutral pH, or other combinations of time, temperature, and pH that are well known in the art to autoclave (or terminally sterilize) an injectable drug.

A method that is an embodiment of the invention includes the steps of treating a polysaccharide with a reducing agent such a borohydride salt or with hydrogen in the presence of an appropriate hydrogenation catalyst such Pt or Pd to obtain the reduced polysaccharide, such that the terminal reducing sugar has been reduced to give an open chain polyhydric structure. The reduced polysaccharide may be an arabinogalactan, a starch, a cellulose, an hydroxyethyl starch (HES), an inulin or a dextran. Moreover, the polysaccharide may be further functionalized prior to particle formation. The method further comprises mixing the reduced polysaccharide with iron salts in an acidic solution selected from the group comprising ferric salts, ferrous salts, or a mixture of ferrous and ferric salts, cooling the solution, neutralizing the solution with a base, and recovering the coated iron oxide colloid.

In accordance with a further embodiment of the invention, the bases which may be employed are sodium hydroxide, sodium carbonate and more preferably, ammonium hydroxide, for the step of neutralizing the colloid. In a further embodiment of the invention, the polysaccharide derivative is reduced dextran and the iron salts may be ferrous and ferric salts, which produce a superparamagnetic iron oxide colloid with a water soluble coating that does not dissociate from the iron oxide core under heat stress during terminal sterilization.

In another embodiment of the invention, only ferric salts are employed, yielding a non-superparamagnetic particle.

In another embodiment, a coated colloid may be prepared by adding a polysaccharide to an iron oxide sol (a colloidal dispersion in a liquid), adjusting the pH to 6–8 and recovering the coated iron oxide colloid.

The term "colloid" as used in this specification and the accompanying claims shall include any macromolecule or particle having a size less than about 250 nm. The iron oxide polysaccharide colloids of the invention have substantially improved physical characteristics and manufacturability compared to previously described materials. Improved physical characteristics are evident in the ability of the colloid to withstand heat stress, as measured by subjecting the colloid to a temperature of 121° C. for 30 minutes. Colloid particles made according to the invention show less evidence of polysaccharide dissociation under stress, remaining colloidal, and exhibiting no appreciable change in size.

During manufacture, the process that is an embodiment of the invention typically uses one tenth or less the amount of polysaccharide compared to the amount required in previous preparations using non-reduced polysaccharide, resulting in substantial raw materials cost savings due to the improved efficiency of the process of the invention.

Variation in such factors as polysaccharide derivative concentration, base concentration and/or Fe(III)/Fe(II) concentration can produce colloids with different magnetic susceptibilities and sizes. Changing the Fe(III)/Fe(II) ratios changes the particle size and alters the magnetic susceptibility. Higher ratios (for example, 2.0 mol/mol) tend to decrease susceptibility, whereas lower ratios (for example, less than 1.5 mol/mol) tend to increase particle size.

The process may be adjusted to yield colloids with different biological properties by changing the type of polysaccharide, and further derivatizing the particle after synthesis.

The colloids that are an embodiment of the invention can be used as contrast agents for magnetic resonance imaging (MRI) or in other applications such as magnetic fractionation of cells, immunoassays, magnetically targeted drug delivery, and as therapeutic injectable iron supplements. These colloids are particularly suited to parenteral administration, because the final sterilization typically is autoclaving, a preferred method since it eliminates viability of all cellular life forms including bacterial spores, and viruses. Previous methods for making colloids required the addition of excipients such as citrate or low molecular weight polysaccharides as stabilizers during the autoclaving process (see U.S. Pat. Nos. 4,827,945 and 5,102,652), or avoided heat stress altogether by use of filter sterilization (see U.S. Pat. No. 5,150,726). Thus, the embodiments of the present invention comprising the colloid compositions, provide utilities as significantly improved MRI contrast agents, and hematinic agents that are iron supplements. The improvements provided in these agents over prior art are found in the following facts demonstrated in the examples herein: that the agents which are embodiments of the present invention are heat sterilizable by autoclaving, and are thus optimized for long-term storage at ambient temperatures; that these agents do not require the addition of excipients for maintenance of stability during the sterilization or storage processes; that the agents are non-toxic to mammals including humans at higher doses; that an effective dose of the agents used for imaging is a smaller amount of material than the agents described in the art; and that the pharmacokinetics following administration are such that iterated successive doses administered after a brief interval after administration of a first dose can be used to obtain additional images during a single clinical visit and use of the imaging apparatus.

In the case of dextran and derivatives thereof, the formulations prepared by this method are less immuno-responsive in mammals, as shown by data obtained using a rat model, and in clinical trials in human subjects. The dextran- and dextran derivative-coated iron particles enhanced imaging of the heart, lungs, kidneys, and other organs and systems in three mammalian species: rat, pig, and human. The dextran- and dextran derivative-coated iron particles can be used also as hematinic agents, to provide iron in a more efficiently absorbed format than is true of oral iron supplements, to groups of patients who are chronically iron-deprived, such as dialysis patients, cancer patients, gastroenteritis patients, and recipients of erythropoietin. The derivatized reduced dextrans can be used also as plasma extenders, which, unlike blood and blood fractions, do not have to be cross-matched immunologically, and unlike human serum albumin preparation, can be sterilized in a manner that destroys viruses, including strains of hepatitis, CMV, and HIV, spongiform encephalitis, and other infectious agents. The plasma extenders of the invention do not have to be refrigerated or stored away from light and heat, and are thus advantageous in emergency medical situations, such as treatment of shock due to loss of blood such as trauma, even in tropical climates.

Examples 1, 2 and 3 show the methods for making reduced dextrans of type T1, T5, and T10, respectively. Example 4 describes preparation of reduced pullulan.

Examples 5–9 describe the synthesis of carboxymethyl reduced dextran T10 with varying degrees of carboxymethylation, from native dextran T10. (Table 2).

Examples 10–15 describe the synthesis of carboxymethyl reduced dextran T10 with varying degrees of carboxymethylation, starting with reduced dextran T10 (Table 3).

Examples 16–18 describe the synthesis of carboxymethyl dextran T10, T40, and T70 from native dextran.

Examples 19–26 describe the preparation of reduced and native dextran coated iron oxides. The conditions of the reactions in these examples were chosen to yield USPIOs coated either with reduced or non-reduced polysaccharides. The reactions conditions for the native dextran iron oxide preparations were the same as for the reduced dextran preparations of the same molecular weights, to allow comparison of the effectiveness of the respective dextrans in coating particles. Mean volume diameter (MVD) and magnetic susceptibility of iron oxide preparations obtained using reduced in comparison to native polysaccharides (prepared in these examples) are summarized in Table 4.

Examples 27–29 describe a procedure for the preparation of USPIOs with native T1, T5, and T10 dextrans, to obtain iron oxide colloids having a particle diameter of less than 30 nm. A comparison of effects of native dextrans (Examples 27–29) and their respective reduced dextrans (Examples 19, 21, and 23) in the synthesis and properties of iron oxide colloids is shown in Table 5.

Examples 30–31 describe the preparation USPIOs coated with carboxymethyl native dextran T10 and carboxymethyl reduced dextran T10.

Examples 32–41 describe the preparation of USPIOs coated with carboxymethyl reduced dextran T10 preparations containing varying extents of carboxymethylation. The effect of extent of carboxymethylation of CMRDs on colloid size of USPIOs is shown in Table 6. The effect of extent of carboxymethylation of CMRDs on solubility of ferric/ferrous chloride solutions is shown in Table 7.

Examples 42–48 describe the synthesis of iron oxide sols and their stabilization with native and reduced dextrans and CMRD. Example 49 describes preparation of CMRD coated non-magnetic iron oxide colloid using base precipitation of ferric chloride and CMRD.

Example 50 examines the effect of the process of sterilization by autoclaving of various preparations of USPIOs coated with reduced and native dextrans on the properties of these particles. The results are shown in Tables 8 and 9.

Example 51 reports the relaxation properties of various contrast agents comparing these properties for gadolinium based contrast agents and USPIOs prepared with native dextran and carboxymethyl reduced dextran T10 (Table 10).

In Examples 52–53, the presence of symtoms of toxicity to rats at doses in vast excess of reduced and non-reduced (native) dextran coated USPIOs was determined, with response to an anaphylactic type reaction. The extent of the anaphylatic type reaction is determined by volume of paw edemia. Similar studies were performed using native, reduced, and carboxymethylated reduced dextrans. The result are summarized Tables 11–14.

Figure 4:
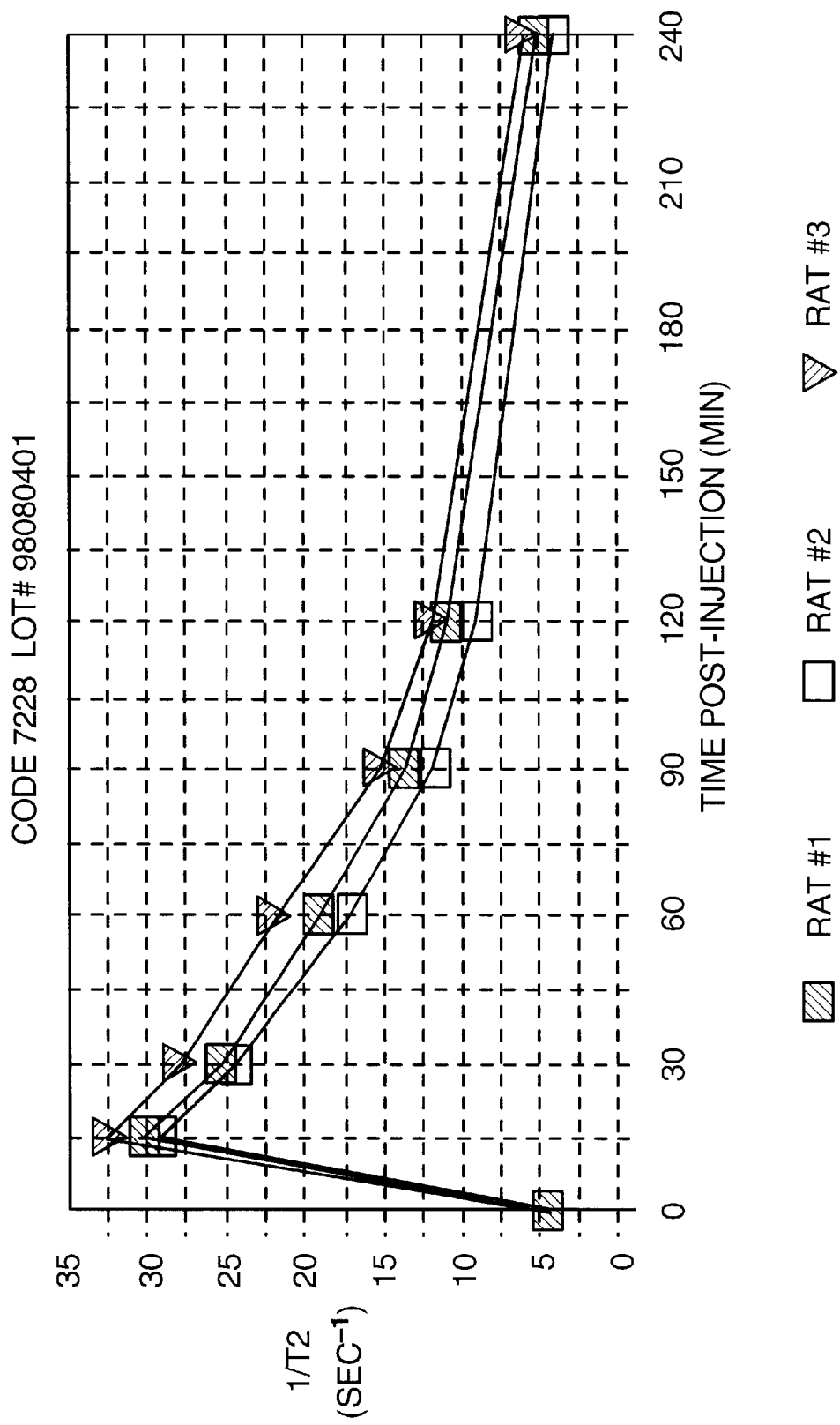
FIG. 4 shows pharmacokinetics of CMRD coated USPIO in the blood of three male rats following intravenous administration of 2.2 mg of iron per kg body weight. Samples (0.25 ml) of blood were collected at the times indicated on the abcissa, and relaxation times were measured on a Brucker Minispec spectrometer.
Figure 5:
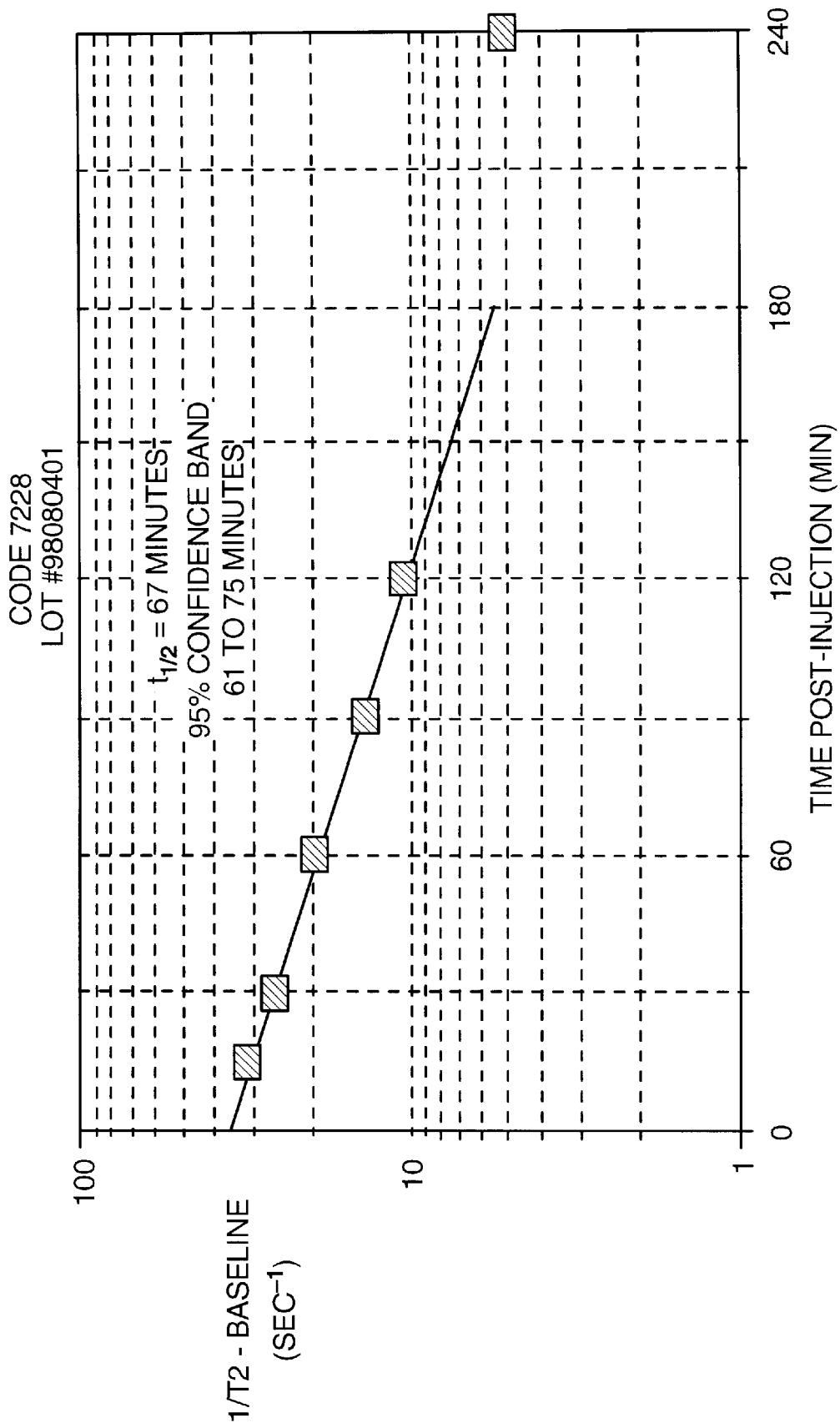
FIG. 5 shows the graph used to determine a half-life (67 minutes) of CMRD coated USPIO in rat blood. The data of FIG. 4 were used to generate the graph in FIG. 5. The half-life range of 61 to 75 minutes was within the 95% confidence level.

Example 54 and FIGS. 4 and 5 show the kinetics of clearance of a CMRD coated USPIO from rat circulation. The half-life of the agent is determined.

Figure 6A:
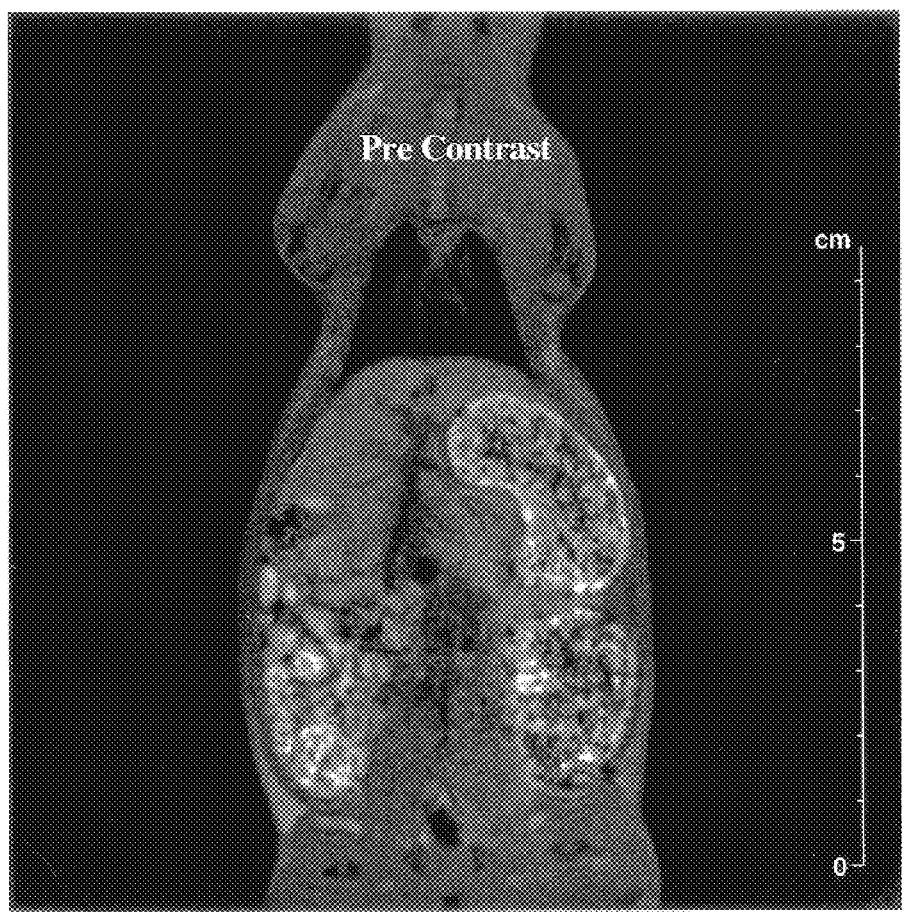
FIG. 6 shows MRIs of a rat, pre-administration (A) and post-administration (B) of contrast agents, anterior portion at top. CMRD coated USPIO (5 mg of iron per kg body weight) was administered into the femoral vein prior to taking the post administration contrast image. The figure illustrates enhanced visualization of the heart and surrounding arteries and veins caused by administration of CMRD coated USPIO. Imaging was performed using a General Electric 2 Tesla magnetic resonance imager.

An enhanced MRI scan is shown in Example 55 and FIG. 6 following administration of CMRD coated USPIO, the scan showing images of the rat heart, aorta and other cardiac-associated arteries. Example 56 and FIG. 7 show a CMRD coated USPIO enhanced MRI scan of the anterior portion of a pig. Example 57 shows that injection of CMRD coated USPIOs into human subjects, as part of a clinical trial, produced no adverse effects. Example 57 describes the biodistribution (FIG. 8), imaging kinetics (FIG. 9 and Table 15), and absence of background in MRI usage of this material in humans. The data in this example show the ability of the practitioner of the invention to perform multiple administrations and obtain subsequent images within the real time of an office visit or visit to a MRI facility.

EXAMPLES

General Procedures for the Synthesis of Reduced Polysaccharides

Reduced polysaccharides were prepared by treatment with excess sodium borohydride and generally purified using five cycles of ultrafiltration. Distilled water is used throughout the examples. In the case of the polysaccharide pullulan, the reduction mixture was used without further purification. In all cases, the products showed less than 5% residual aldehyde content Residual aldehyde concentration was determined using a modified tetrazolium blue assay (Jue, C. K. et al., *J. Biochem. Biophys. Methods,* 1985, 11:109–15). Dextran concentration was determined by a phenol/sulfuric acid assay (Kitchen, R., *Proc. Sugar Process. Res. Conf.,* 1983, 232–47). In cases where ultrafiltration was omitted, it was demonstrated that, except for the dextran T1, the residual borate salts did not affect particle formation. Examples 1 through 4 provide methods of synthesis of reduce polysaccharides T1, T5, and T10 dextrans, and pullulan, respectively. Retention times were determined using a Waters Ultrahydrogel 250 column, SN T52262A33, with 20 mM phosphate buffered saline, 0.4 ml/min flow rate.

Example 1

Reduced Dextran T1

Dextran T1 (10 g) was dissolved in 100 ml water at 25° C., 1.0 g of sodium borohydride was added, and the mixture was stirred for 12 h. The pH was brought to 5.0 using 6 M HCl, and 200 ml ethanol (anhydrous) was added. The precipitate was collected by centrifugation. The ethanol/water layer was decanted, and the residue was dissolved in 100 ml water. Addition of 200 ml of absolute ethanol was used to cause a second precipitation, and the ethanol/water was again decanted. The precipitated product was dissolved in water, and was lyophilized to produce a white solid, with a 60% yield. The observed HPLC retention times (min) were: for reduced dextran, 24.4; and for native dextran, 24.4.

Example 2

Reduced Dextran T5

Dextran T5 (4 g) was dissolved in 25 ml water at 25° C., 83 mg of sodium borohydride was added, and the mixture was stirred for 12 h. The pH was brought to 5.0 using 6 M HCl. The mixture was ultrafiltered against a 1 kDa molecular weight cut-off (MWCO) membrane filter. The product was lyophilized to produce a white solid, and a 70% yield was obtained. The observed HPLC retention times (min) were: for reduced dextran, 22.9; for native dextran, 21.9.

Example 3

Reduced Dextran T10

Dextran T10 (5,003 g) was dissolved in 26,011 g water. Sodium borohydride was added (52.5 g) and the mixture was stirred for 24 hours. The pH was adjusted to 7.1 using 6 N HCl. The product was purified by repeated ultrafiltration against a 3 kDa ultrafiltration membrane and lyophilized to produce a white solid. Yield: 3129 g. The observed HPLC retention times (min) were: for reduced dextran, 21.6; for native dextran, 21.1.

Example 4

Reduced Pullulan

Pullulan (90 mg) was dissolved in 0.8 ml water at 25° C., and 1 mg of sodium borohydride was added. The mixture was stirred for 12 h, and was used directly in the preparation of USPIO.

General Procedures for Synthesis of a Carboxymethyl Reduced Dextran Using Native Dextran T-10 as a Substrate Examples 5–9 describe the synthesis of carboxymethyl reduced dextrans from native dextran. Two general methods of synthesis are presented, a low dextran concentration method (Example 5) in which the starting concentration of native dextran was 70 mg/g, and a high dextran concentration method (Examples 6–9), in which the starting concentration of native dextran was 240 mg/g.

Example 5

Carboxymethyl Reduced Dextran T10 Prepared by the Low Dextran Concentration Method The following solutions were prepared and cooled to 5° C.: Solution A contained 4,200 g sodium hydroxide in 10.5 liters of water; and Solution B contained 2,310 g bromoacetic acid in 5,700 ml water. Solution C contained 3,000 g dextran T10 in 7,500 ml water, heated to 38° C.

Sodium hydroxide (600 g) was dissolved in 7.5 liters of water and was warmed to 38° C. Sodium borohydride (60 g) was added and the mixture was stirred for 2 min before adding Solution C, followed immediately by adding a second 60 g portion of sodium borohydride. The mixture was stirred at 38° C. for 30 min, and then cooled to 15° C. Solution A was added, keeping the temperature of the solution below 25° C. Solution B was added, and the temperature of the solution was maintained below 25° C. The mixture was stirred for 2 hours at room temperature, and was neutralized to, pH 7.5 using 6M HCl cooled to 5° C., maintaining the solution temperature below 35° C. The mixture was filtered though a 0.2 μm filter, and diluted to 80 liters. The product was purified by repeated ultrafiltration through a 3 kDa MWCO ultrafiltration membrane, again filtered through a 0.2 μm filter and was lyophilized.

The recovered solid, 2,560 g of carboxymethyl reduced dextran T10 (sodium salt), showed a carboxyl content of approximately 1,265 micromoles carboxyl per gram of product, as determined by titration. The use of bromoacetic acid allowed the reaction to proceed at a lower temperature compared to use of chloroacetic acid, and produced a cleaner product as evidenced by its FTIR spectrum (FIG. 1). FIG. 1 shows no carbonyl absorption other than that of the carboxylate at 1600 cm$^{-1}$, unlike the FTIR of the product in U.S. Pat. No. 5,204,457 which was prepared with chloroacetic acid.

Example 6

Carboxymethyl Reduced Dextran CMRD T10 Prepared by the High Dextran Concentration Method Sodium borohydride (6.4 g) and 0.5 g of a 50% solution weight/weight of sodium hydroxide in water were added to a solution of 25 g dextran in 50 g water. The mixture was stirred 4 hours at room temperature, 19.5 g of the 1:1 sodium hydroxide solution and 6.2 g bromoacetic acid were added, and the temperature was kept below 25° C. using an ice bath. The mixture was then stirred 16 hours at room temperature.

To purify the product, the pH of the mixture was adjusted to pH 6.2 using 6 M HCl, and 120 ml ethanol was added. A precipitate formed and was allowed to settle, and the supernatant was removed by decanting: The residue was dissolved in 60 ml water, and 200 mg sodium chloride was added, followed by 30 ml ethanol, and the carboxymethyl reduced dextran was allowed to settle out. The sequence of addition of water and sodium chloride followed by dissolution of the precipitate and ethanol precipitation, was repeated an additional two times. The residue was dissolved in 60 ml water, and 1 liter of ethanol was added. The carboxymethyl reduced dextran was again allowed to settle out, and the solid was collected on a medium frit glass filter. The white solid was dried 24 hours at 50° C. The yield was 27 g of product having 1108 micromoles carboxyl per gram as measured by titration (Table 2).

Example 7

Carboxymethyl Reduced Dextran T10 Prepared by the High Dextran Concentration Method Sodium borohydride (0.4 g) and 0.5 g of 50% sodium hydroxide were added to a solution of 25 g dextran in 50 g water. The mixture was stirred 4 hours at room temperature, 20.0 g 50% of sodium hydroxide and 6.95 g of bromoacetic acid were added and temperature was kept below 25° C. using an ice bath while the mixture was stirred for 16 hours at room temperature. The product was purified as described in Example 6. The yield was 23.9 g of product having 1262 micromoles carboxyl per gram as measured by titration (Table 2).

Example 8

Carboxymethyl Reduced Dextran T10 Prepared by the High Dextran Concentration Method Sodium borohydride (0.4 g) and 0.5 g of 50% sodium hydroxide were added to a solution of 25 g dextran in 50 g water. The mixture was stirred for 4 hours at room temperature, and 20.67 g of 50% sodium hydroxide and 7.65 g bromoacetic acid were added while the temperature was kept below 25° C. using an ice bath. The mixture was stirred for 16 hours at room temperature. The product was purified as described in Example 6. The yield was 24.5 g of product having 1404 micromoles carboxyl per gram as measured by titration (Table 2).

Example 9

Carboxymethyl Reduced Dextran CMRD T10 Prepared by the High Dextran Concentration Method Sodium borohydride (0.4 g) and 0.5 g of 50% solution of sodium hydroxide were added to a solution of 25 g dextran in 50 g water. The mixture was stirred for 4 hours at room temperature, and 20.67 g of 50% sodium hydroxide and 7.65 g of bromoacetic acid were added while the temperature was kept below 25° C. using an ice bath. The mixture was stirred for 16 hours at room temperature, and the product was purified as described in Example 6. The yield was 23.4 g of product having 1528 micromoles carboxyl per gram of product as measured by titration (Table 2).

Figure 3:
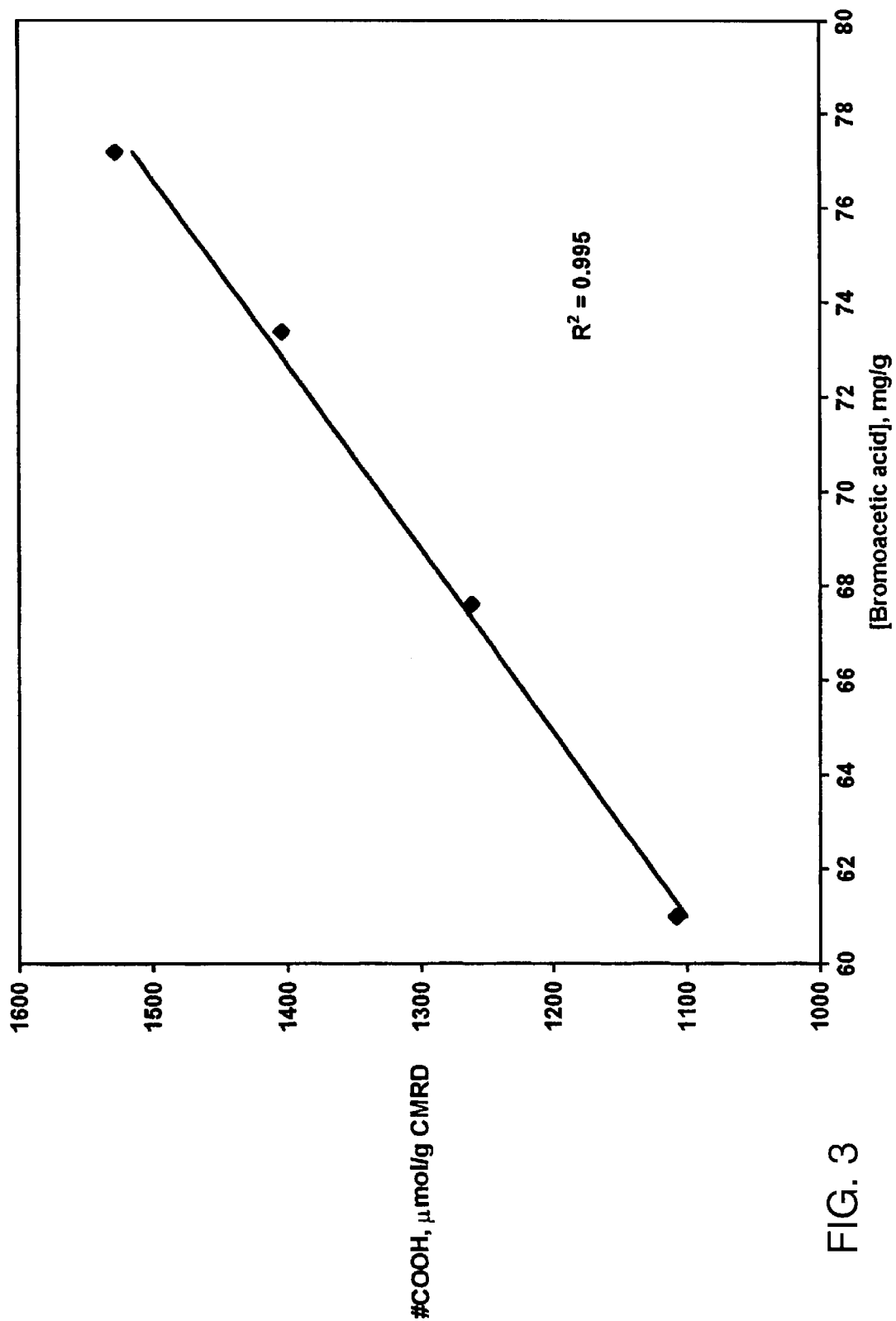
FIG. 3 is a graph that shows the amount of carboxymethyl groups (micromoles) per gram of product, on the ordinate, as a function of the amount of bromoacetic acid mg/gram used in reactions with reduced dextran starting material, on the abscissa. The graph is plotted from the data of Table 2.

The relationship between amount of bromoacetic acid used in the synthesis and the resulting incorporation of micromoles of carboxyl groups into dextran was examined using the high dextran concentration method. The relationship was found to be linear (see Table 2 and FIG. 3). Reactant masses and carboxmethyl yields for Examples 6 through 9 are shown in Table 2.

TABLE 2

| | Conditions for CMRD synthesis extent and degree of carboxymethylation of the product. | | | |
|---|---|---|---|---|
| Example | dextran mg/g | NaOH, mg/g | bromoacetic acid, mg/g | micromoles COOH per g product |
| 6 | 246 | 96.0 | 61.0 | 1108 |
| 7 | 243 | 97.2 | 67.6 | 1262 |
| 8 | 240 | 99.2 | 73.4 | 1404 |
| 9 | 238 | 100.3 | 77.2 | 1528 |

Synthesis of Carboxymethyl Reduced Dextran Preparations Using Reduced Dextran T-10 by the Low Dextran High Base Method Examples 10–14 describe the synthesis of carboxymethyl reduced dextrans with varying degrees of substitution starting with a low concentration of reduced dextran. In this method, the starting concentration of reduced dextran was 70 mg/g and the NaOH was at least about 107 mg/g. Table 3 shows that the extent of carboxymethyl substitution increased as the amount of bromoacetic acid used in the reaction increased.

Example 10

Carboxymethyl Reduced Dextran CMRD T10 Using the Low Dextran High Base Method Reduced dextran T10 (15 g) was dissolved in 72 ml water, and 72 ml of 8M sodium hydroxide was added. The mixture was brought to 25° C., and a solution of 1.15 g bromoacetic acid in 3 ml of water was added. The mixture was stirred at room temperature for 1 hour, and then added to a 75 ml volume of crushed ice. The pH of the solution was brought to pH 6.0 using 6M HCl. After repeated ultrafiltration against a 3 kDa ultrafiltration membrane, the product was lyophilized. The yield was 13.25 g of product. The recovered solid, carboxymethyl reduced dextran T10 (sodium salt), showed a carboxyl content of approximately 110 micromoles carboxyl per gram as determined by titration (Table 3).

Example 11

Carboxymethyl Reduced Dextran T10 Using the Low Dextran High Base Method

Reduced dextran T10 (150 g) was dissolved in 720 ml water, and 720 ml of 8M sodium hydroxide was added. The mixture was brought to 25° C., and a solution of 11.5 g bromoacetic acid in 140 ml water was added. The mixture was stirred at room temperature for 1 hour, added to a 750 ml volume of crushed ice, and the pH of the solution was brought to pH 6.0 with 6M HCl. After repeated ultrafiltration against a 3 kDa MWCO ultrafiltration membrane, the product was lyophilized. The yield was 126.21 g of recovered solid carboxymethyl reduced dextran T10 (sodium salt), having a carboxyl content of approximately 130 micromoles carboxyl per gram product as determined by titration (Table 3).

Example 12

Carboxymethyl Reduced Dextran CMRD T10 Using the Low Dextran High Base Method Reduced dextran T10 (150 g) was dissolved in 720 ml water, and 720 ml of 8M sodium hydroxide was added. The mixture was brought to 25° C., a solution of 26.6 g bromoacetic acid in 140 ml water was added, and the mixture was stirred at room temperature for 1 hour and added to a 750 ml volume of crushed ice. The pH of the solution was brought to pH 6.0 with 6M HCl. After repeated ultrafiltration against a 3 kDa MWCO ultrafiltration membrane, the product was lyophilized. The yield was not determined. The recovered solid, carboxymethyl reduced dextran T10 (sodium salt), showed a carboxyl content of approximately 280 micromoles carboxyl per gram product as determined by titration (Table 3).

Example 13

Carboxymethyl Reduced Dextran CMRD T10 Using the Low Dextran High Base Method Reduced dextran T10 (15 g) was dissolved in 72 ml of water, and 72 ml of 8M sodium hydroxide was added. The mixture was brought to 25° C., and a solution of 3.45 g of bromoacetic acid in 8 ml water was added. The mixture was stirred at room temperature for 1 hour, and then added to a 75 ml volume of crushed ice. The pH of the solution was brought to pH 6.0 with 6M HCl. After repeated ultrafiltrations against 3 kDa MWCO ultrafiltration membranes, the product was lyophilized. The yield was 9.4 g of recovered solid carboxymethyl reduced dextran T10 (sodium salt), having a carboxyl content of approximately 450 micromoles carboxyl per gram product as determined by titration (Table 3).

Example 14

Carboxymethyl Reduced Dextran CMRD T10 Using the Low Dextran High Base Method Reduced dextran T10 (150 g) was dissolved in 720 ml of water, and 720 ml of 8M sodium hydroxide was added. The mixture was brought to 25° C., and a solution of 58.8 g of bromoacetic acid in 140 ml water was added. The mixture was stirred at room temperature for 1 hour, and was then added to a 750 ml volume of crushed ice. The pH of the solution was brought to pH 6.0 using 6M HCl. After repeated ultrafiltrations against a 3 kDa MWCO ultrafiltration membrane, the product was lyophilized. The yield was 127.88 g of the recovered solid carboxymethyl reduced dextran T10 (sodium salt), having a carboxyl content of approximately 580 micromoles carboxyl per gram product as determined by titration (Table 3).

Table 3 shows that the extent of carboxymethyl substitution observed was a function of the amount of bromoacetic acid used in the reaction. The data show that generally increasing the amount of bromoacetic acid in the reaction resulted in increasing levels of COOH in the product. The yield of carboxymethyl incorporation was also affected by conditions such as scale of the reaction, for example, as in Examples 13 and 14.

TABLE 3

Preparation of CMRDs with varying extents of carboxymethylation.

| Example | dextran mg/g | NaOH mg/g | bromoacetic acid mg/g | micromoles COOH/g product |
|---|---|---|---|---|
| 10 | 75 | 115.7 | 5.77 | 110 |
| 11 | 75 | 115.7 | 5.77 | 130 |
| 12 | 73 | 111.6 | 16.7 | 280 |
| 13 | 70 | 107.2 | 27.3 | 450 |
| 14 | 70 | 107.2 | 27.3 | 580 |

Example 15

Carboxymethyl Reduced Dextran T10 from a Commercial Source

Carboxymethyl reduced dextran was purchased from Amersham-Pharmacia. The solid showed a carboxyl content of approximately 1887 micromoles carboxyl per gram product as determined by titration.

Examples 16–18 describe synthesis of carboxymethyl dextran from native, non-reduced dextran T-10, T-40, and T-70, respectively.

Example 16

Carboxymethyl Dextran T10

The following solutions were prepared and cooled to 5° C.: Solution A: 105.2 g sodium hydroxide in 250 ml water; Solution B: 58.0 g bromoacetic acid in 142.5 ml water; and Solution C: 75.7 g dextran T10 in 187.5 ml water.

To Solution C and Solution A were added sodium hydroxide (14.4 g) dissolved in 187.5 ml water while maintaining the temperature of the solution below 25° C. Solution B was added, keeping the temperature below 25° C., and the resulting solution was stirred for 2 hours at room temperature, then was neutralized to pH 7.5 with 6M HCl (cooled to 5° C.) while maintaining the solution temperature below 35° C. The mixture was passed through a 0.2 µm pore size filter, and diluted to 2 liters. The product was purified by repeated ultrafiltration against a 3 kDa MWCO ultrafiltration membrane, 0.2 µm filtered again, and lyophilized. The yield was 53.17 g, and the recovered solid carboxymethyl dextran T10 (sodium salt) showed a carboxyl content of approximately 1220 micromoles carboxyl per gram product as determined by titration.

Example 17

Carboxymethyl Dextran T40

The following solutions were prepared and cooled to 5° C.: Solution A: 154 g sodium hydroxide in 480 ml water; Solution B: 77 g bromoacetic acid in 260 ml water; and Solution C: 100 g dextran T40 in 400 ml water.

Solution A was added to Solution C all at once. After 5 min, Solution B was added and the combined solution was stirred for 120 min while the temperature was maintained between 20° C. and 25° C. The mixture was neutralized with 6 M HCl, was 0.2 µm filtered, and diluted to 2 liters. The product was purified by repeated ultrafiltration against 3 kDa MWCO ultrafiltration membranes, was 0.2 µm filtered, and was lyophilized. The yield was 105.1 g of recovered solid carboxymethyl dextran T40 (sodium salt), which showed a carboxyl content of about 1390 micromoles carboxyl per gram product as determined by titration.

Example 18

Carboxymethyl Dextran T70

The following solutions were prepared and cooled to 5° C.: Solution A: 154 g sodium hydroxide in 480 ml water; Solution B: 77 g bromoacetic acid 260 ml water; and Solution C: 100 g dextran T70 in 400 ml water.

Solution A was added to Solution C all at once. After 5 min, Solution B was added, and the combined solution was stirred, maintaining the temperature between 20° C. and 25° C. using an ice bath. After 120 min, the solution was neutralized with 6 M HCl. The solution was 0.2 µm filtered, and diluted to 2 liters. The product was purified by repeated ultrafiltration against 3 kDa MWCO ultrafiltration membranes, was 0.2 µm filtered again and was lyophilized. The yield was 106.9 g of recovered solid carboxymethyl dextran T70 (sodium salt), having a carboxyl content of about 1380 micromoles carboxyl per gram product as determined by titration.

General Procedure for the Preparation of Superparamagnetic Colloids for Comparison of the Properties of USPIO Preparations Coated with Either of Reduced or Non-reduced Polysaccharides Examples 19–26 were conducted to compare polysaccharide coated iron oxide products obtained from pairs of native and reduced polysaccharides of identical molecular weights. Identical procedures were utilized for the preparation of USPIO colloids for each pair of native and reduced polysaccharide of identical molecular weight. In particular, the same polysaccharide to iron ratio and iron concentration was used for each molecular weight pair. The polysaccharide to iron ratio and iron concentration utilized for each native and reduced polysaccharide pair were chosen to yield a 0.2 µm filterable USPIO with a diameter of less than 30 nm and a magnetic susceptibility of greater than 20,000×10$^{-6}$ cgs with the reduced polysaccharide.

The general procedure involved addition of excess ammonium hydroxide to a solution of iron salts ($Fe^{+3}/Fe^{+2}$) and polysaccharide, followed by heating, and performing six cycles of ultrafiltration against water using a 100 kDa MWCO membrane filter. After ultrafiltration, the USPIO preparations formed with reduced polysaccharide were filtered through a 0.2 µm filter and stored at 4° C.

It was observed that for iron oxides prepared with a native polysaccharide, only the native dextran T10 coated iron oxide was filterable through a 0.2 µm filter. The size and magnetic susceptibility, except for those samples containing particulate materials, were then measured. Particle sizes were determined by measurement of dynamic light scattering in a Microtrac® UPA instrument (Honeywell IAC Microtrac, Fort Washington, Pa.) and are reported as the mean volume diameter (MVD). Magnetic susceptibility was determined with a Mathey Johnson magnetic susceptibility balance. Iron concentrations were determined with a bipyridyl assay (Kumar K., *J. Liq. Chromatogr. Relat. Technol.*, 1997, 20, 3351–3364).

Example 19

Preparation of Reduced Dextran T1 Coated USPIO

Reduced dextran T1 (1.7 g) was dissolved in 20 ml water, and a solution of 3 g of ferric chloride hexahydrate and 1.5 g of ferrous chloride tetrahydrate in 32 g water was added. The mixture was purged with nitrogen for 30 min, cooled to 5° C., and 12.7 g of 28% ammonium hydroxide was added with stirring during a 2 min period. The mixture was heated to 60° C., maintained at this temperature for 40 min, then incubated at 80° C. for 2 h. The product was subjected to six cycles of ultrafiltration against water using a 100 kDa MWCO membrane filter. After ultrafiltration, the product was filtered through a 0.2 µm filter and stored at 4° C. The product was observed to have the following properties: the mean volume diameter (determined by use of a Microtrac Particle Size Analyzer) was 18 nm; the magnetic susceptibility was 13,323×10$^{-6}$ cgs/g Fe.

Example 20

Preparation of Native Dextran T1 Coated Iron Oxide

Native dextran T1 iron oxide was prepared by the method described above for the reduced dextran in Example 19 except that native dextran T1 was used instead of reduced dextran T1. The product was observed to have the following properties: the mean volume diameter (determined by use of a Microtrac Particle Size Analyzer) was 2764 nm; the magnetic susceptibility was 1,953×10$^{-6}$ cgs/g Fe.

Example 21

Preparation of Reduced Dextran T5 Coated USPIO

Reduced dextran T5 (0.45 g) was dissolved in 13 ml water, and a solution of 0.5 g of ferric chloride hexahydrate and 0.25 g of ferrous chloride tetrahydrate in 4.5 g water was added. The mixture was purged with nitrogen for 30 min, cooled to 5° C., and 1.42 g of 28% ammonium hydroxide was added with stirring during a 2 min period. The mixture was heated at 80° C. for 2 h, and was purified as described in Example 19. The product was observed to have the following properties: the mean volume diameter (determined by use of a Microtrac Particle Size Analyzer) was 16 nm; the magnetic susceptibility was 33,943×10$^{-6}$ cgs/g Fe.

Example 22

Preparation of Native Dextran T5 Coated Iron Oxide

Native dextran T5 iron oxide was prepared by the method described above for the reduced dextran in Example 21 except that native dextran T5 was used instead of reduced dextran T5. The product was observed to have the following properties: the mean volume diameter (determined by use of a Microtrac Particle Size Analyzer) was 1,916 nm.

Example 23

Preparation of Reduced Dextran T10 Coated USPIO

Reduced dextran T10 (2.7 g) was dissolved in 70 ml water, and a solution of 2.0 g ferric chloride hexahydrate and 1.0 g ferrous chloride tetrahydrate in 27 g water was added. The mixture was purged with nitrogen for 30 min, cooled to 5° C., and 8.5 g of 28% ammonium hydroxide was added with stirring during a 2 min period. The mixture was heated at 80° C. for 2 h and purified as described in Example 19. The product was observed to have the following properties: the mean volume diameter (determined by use of a Microtrac Particle Size Analyzer) was 12 nm; the magnetic susceptibility was $31,743 \times 10^{-6}$ cgs/g Fe.

Example 24

Preparation of Native Dextran T10 Coated Iron Oxide

Native dextran T10 iron oxide was prepared by the method described above for the reduced dextran in Example 23 except that native dextran T10 was used instead of reduced dextran T10. The product was observed to have the following properties: the mean volume diameter (determined by use of a Microtrac Particle Size Analyzer) was 757 nm; the magnetic susceptibility was $31,252 \times 10^{-6}$ cgs/g Fe.

Example 25

Preparation of Reduced Pullulan Coated USPIO

Reduced pullulan (0.045 g) was dissolved in 0.4 ml water, and a solution of 0.106 g ferric chloride hexahydrate and 0.05 g ferrous chloride tetrahydrate in 1.3 g water was added. The mixture was purged with nitrogen for 30 min, cooled to 5° C., and 0.044 g of 28% ammonium hydroxide was added with stirring during a 2 min period. The mixture was heated at 80° C. for 0.67 h and purified as described in Example 19. The product was observed to have the following properties: the mean volume diameter (determined by use of a Microtrac Particle Size Analyzer) was 20 nm; the magnetic susceptibility was $27,066 \times 10^{-6}$ cgs/g Fe.

Example 26

Preparation of Native Pullulan Coated Iron Oxide

Native pullulan iron oxide was prepared by the method described above for the reduced pullulan in Example 25 except that native pullulan was used instead of reduced pullulan. The product was observed to have the following properties: the mean volume diameter (determined by use of a Microtrac Particle Size Analyzer) was 1,184 nm.

Properties of Iron Oxide Preparations Obtained Using Reduced in Comparison to Native Polysaccharides (Comparison of Data Obtained from Examples 19–26)

In general for MRI contrast agents, an iron oxide contrast agent particle of small size is preferred, for example, a particle having a diameter in the range of 10 to 50 nm. Further, an iron oxide of greater magnetic susceptibility, and of greater homogeneity is preferred.

It is observed from the data of Examples 19–26 that the presence of a reduced terminal sugar of a polysaccharide (reduced polysaccharide) used to coat an iron oxide had an unexpected and substantial effect on the diameter of particles of each of the resulting colloids, compared to similarly produced iron oxides made using native non-reduced polysaccharide. Table 4 shows the size of particles formed for each pair of native and reduced polysaccharides, as indicated by the mean volume diameters (MVD). The concentration of reduced and native polysaccharides were kept constant within each molecular weight group. Concentrations were selected to optimize the synthesis of USPIO with reduced polysaccharide. For all polysaccharides, use of the native non-reduced polysaccharide consistently produced a larger particle than did use of the reduced dextran, so that the reduced polysaccharide consistently gave the preferred smaller particle.

Further, for each pair of polysaccharides of a given molecular weight that was synthesized and tested, the USPIO preparation coated with reduced polysaccharides demonstrated a higher magnetic susceptibility value than the corresponding iron oxide preparation synthesized with native polysaccharide, except for colloids obtained with dextran T10 for which magnetic susceptibilities of reduced and native coatings were equivalent.

These data indicate that use of a reduced polysaccharide in preparation of coated USPIO colloids yields preferred particles of small size, without loss of magnetic susceptibility. The data demonstrate the surprising effect that reduction of the aldehyde of a polysaccharide has upon the synthesis of a polysaccharide-coated USPIO.

TABLE 4

Comparison of properties of iron oxides made with native or reduced polysaccharides under conditions that form a USPIO with reduced polysaccharides.

| Example | polysaccharide | ratio of polysaccharide per Fe, g/g | MVD nm reduced | MVD nm native | MS[a] reduced | MS[a] native |
|---|---|---|---|---|---|---|
| 19, 20 | dextran T1 | 1.6 | 18 | 2,764 | 13,323 | 1,953 |
| 21, 22 | dextran T5 | 2.9 | 16 | 1,916 | 33,943 | [b] |
| 23, 24 | dextran T10 | 4.6 | 21 | 757 | 31,743 | 31,252 |
| 25, 26 | pullulan | 3.9 | 20 | 1,184 | 27,066 | [b] |

[a]Magnetic susceptibility ($\times 10^{-6}$ cgs/g Fe)
[b]The sample was particulate, could not be filtered through a 0.2 μm filter, and magnetic susceptibility was not determined.

Properties of Iron Oxides Prepared with Native Non-reduced T1, T5 and T10 Dextrans of Mean Volume Diameter Less than 30 nm Examples 27 through 29 show the preparation of iron oxides obtained from native dextran T1, T5, and T10. Colloids were prepared using non-reduced (native) dextrans as described for reduced dextrans (Examples 19, 21, and 23), except that the preparation of these native non-reduced dextran particles required about 10- to 34-fold more dextran than their corresponding reduced dextran counterpart to produce iron oxides of corresponding size. The requirement for increased dextran usage is shown by comparing the dextran to iron ratio of the products for corresponding molecular weight pairs of iron oxides shown (Table 5).

The data show that the magnetic properties, and the efficiency of dextran use during synthesis, of iron oxide particles prepared with each of native dextrans T1, T5, and T10 were inferior compared with corresponding properties of particles prepared with each counterpart reduced dextran.

Examples 27

Preparation of Iron Oxide Coated with Native T1 Dextran

A mixture of 0.42 g ferric chloride hexahydrate, 0.21 g ferrous chloride tetrahydrate, and 7.27 g water was filtered through a 0.2 μm filter. A 1.0 g portion of this mixture was added to 10 ml of an aqueous solution of 0.1 g dextran T1/g water. The mixture was purged with nitrogen before adding 0.22 ml of 28% ammonium hydroxide solution. The mixture was heated at 80° C. for 1 hour, cooled to room temperature and filtered through a 0.2 μm filter. The product was observed to have the following properties: the mean volume diameter (determined by use of a Microtrac Particle Size Analyzer) was 27 nm; the magnetic susceptibility was $2325 \times 10^{-6}$ cgs/g Fe.

Examples 28

Preparation of Iron Oxide Coated with Native T5 Dextran

Dextran T5 (0.8 g) was dissolved in 9 ml water, and added to 0.63 ml of a 0.2 μm filtered solution of 51.8 mg ferric chloride hexahydrate and 25.9 mg ferrous chloride tetrahydrate in 9.2 ml water. The mixture was purged with nitrogen before adding 1.4 ml 28% ammonium hydroxide solution. The mixture was heated at 80° C. for 1 hour, cooled to room temperature, and filtered through a 0.2 μm filter. The product was observed to have the following properties: the mean volume diameter (determined by use of a Microtrac Particle Size Analyzer) was 20 nm; the magnetic susceptibility was $1285 \times 10^{-6}$ cgs/g Fe.

Examples 29

Preparation of Iron Oxide Coated with Native T10 Dextran

Dextran T10 (9420 g) was dissolved in 14915 g water. A 14915 g portion of this mixture was filtered through a 0.2 μm filter, and added to the reaction vessel. Ferric chloride hexahydrate (891 g) was dissolved in 713 g water. A 1129 g portion was 0.2 μm filtered and added to the reaction vessel containing the dextran. The mixture was cooled to 5° C. with stirring overnight while bubbling nitrogen through the mixture. Before the last 30 min. of the nitrogen purge, a 580 g portion of a 0.2 μm filtered solution of 359 g ferrous chloride tetrahydrate in 477 g water was added. To this mixture was added 786 g of 28% ammonium hydroxide solution, cooled to 5° C. The mixture was heated to 80° C., incubated at 80° C. for 2 hours, and then poured into 80 liters of water heated to 80° C. The mixture was allowed to cool overnight, 0.2 μm filtered, and purified by ultrafiltration using a 100 kDa ultrafiltration membrane. The product was 0.2 μm filtered. The product was observed to have the following properties: the mean volume diameter (determined by use of a Microtrac Particle Size Analyzer) was 21 nm; the magnetic susceptibility was $32,712 \times 10^{-6}$ cgs/g Fe.

TABLE 5

Magnetic susceptibility and particle size properties of polysaccharide coated iron oxides: a comparison of native dextrans (Examples 27–29) with respective reduced dextrans (Examples 19, 21, and 23) under conditions to give particles of less than 30 nm MVD with maximum magnetic susceptibility

| Example | dextran type | dextran/Fe (g/g)[b] | MVD (nm) | MS[a] |
|---|---|---|---|---|
| iron oxides prepared with native dextran | | | | |
| 27 | dextran T1 | 55 | 27 | 2,325 |
| 28 | dextran T5 | 44 | 20 | 1,285 |
| 29 | dextran T10 | 44 | 21 | 32,712 |
| iron oxides prepared with reduced dextran | | | | |
| 19 | dextran T1 | 1.6 | 18 | 13,323 |
| 21 | dextran T5 | 2.9 | 16 | 33,943 |
| 23 | dextran T10 | 4.6 | 12 | 31,743 |

[a]Magnetic susceptibility ($\times 10^{-6}$ cgs/g Fe)
[b]The polysaccharide/Fe ratio was varied for each dextran in order to obtain a USPIO with a MVD of less than or equal to 30 nm.

Preparation USPIOs Coated with Carboxymethyl Native Dextran T10 and Carboxymethyl Reduced Dextran T10 Containing Varying Degrees of Carboxymethylation Examples 30 and 31 describe preparation of USPIO coated with carboxymethyl native and reduced dextran T10, respectively. Examples 32–36 describe the synthesis of USPIO compositions coated with carboxymethyl reduced dextran T10 preparations, containing varying degrees of carboxymethylation. Examples 37–41 describe the solubility of preparations containing ferric chloride and carboxymethyl reduced dextran T10 containing varying degrees of carboxymethylation.

Example 30

Preparation of USPIO Coated with Carboxymethyl Dextran T10

Carboxymethyl dextran T10 (60 g, prepared by the method Example 16) was dissolved in 532 g water. A solution of 14.7 g ferric chloride hexahydrate, 7.2 g ferrous chloride tetrahydrate, and 100 ml water, was filtered through a 0.2 μm, and added. The mixture was cooled to 10° C., purged with nitrogen, and 52.2 ml of 28% ammonium hydroxide solution was added with stirring. The mixture was heated to 75° C., maintained at 75° C. for 30 min, diluted with 2.5 liter water, and filtered through a 0.2 μm filter. The product was purified by repeated ultrafiltration against a 100 kDa MWCO membrane, concentrated to 20 mg Fe/ml, and again filtered through a 0.2 μm filter. The product was observed to have the following properties: MVD (determined by use of a Microtrac Particle Size Analyzer) was 19 nm; the magnetic susceptibility was $27,835 \times 10^{-6}$ cgs/g Fe; and the carboxyl content was 1,220 micromoles per gram of the CMRD. To determine stability in response to autoclaving, a sample of the product was placed in a sealed 5 ml glass vial, and heated to 121° C. for 30 min (see Table 9).

Example 31

Preparation of USPIO Coated with Carboxymethyl Reduced Dextran T10

Reduced carboxymethyl dextran T10 (40 g prepared in Example 5) was dissolved in 1,038 ml water and was filtered through a 0.2 μm pore size filter. A 0.2 μm filtered solution of 30 g ferric chloride hexahydrate and 15 g of ferrous chloride tetrahydrate in 374 ml of water was added to the dextran, with a 31 ml water wash. The solution was cooled to 10° C., and 114 g of 28% ammonium hydroxide was added. The colloidal mixture was heated to 78° C. and maintained at that temperature for one hour. The solution was then diluted to 3 liter with water, cooled to 10° C., and ultrafiltered 6 times with a YM-100 filter membrane (100 kDa MWCO). A final concentration of 21.1 mg Fe/g was obtained. The product was observed to have the following properties: the mean volume diameter (Microtrac Particle Size Analyzer) was 21 nm; the magnetic susceptibility was $32,732 \times 10^{-6}$ cgs/g Fe; and the carboxyl content was 1,265 micromoles per gram of the CMRD. The content of the particle was determined to be about 50% Fe and 50% dextran. To determine stability in response to autoclaving, a sample of the product was placed in a sealed 5 ml glass vial, and heated to 121° C. for 30 min (see Table 9).

Example 32

Preparation of USPIO Coated with Carboxymethyl Reduced Dextran T10 Having 110 Micromoles Carboxyl per Gram Carboxymethyl reduced dextran T10 (4 g, prepared in Example 10) was dissolved in 85 ml water. To this was added a 0.2 μm filtered mixture of 2.99 g ferric chloride hexahydrate, 1.49 g ferrous chloride tetrahydrate, and 37.3 ml water. The mixture was cooled to 10° C., purged with nitrogen, 11.4 g of 28% ammonium hydroxide solution was added with stirring the mixture was heated to 90° C., maintained at 78° C. for 60 minutes, and then maintained at 78° C. while bubbling air through the mixture. The mixture was diluted with 1.5 liters of water, and was filtered through a 0.2 μm filter. The product was purified by repeated ultrafiltration against a 100 kDa MWCO membrane and again filtered through a 0.2 μm filter.

Example 33

Preparation of USPIO Coated with Carboxymethyl Reduced Dextran T10 Having 130 Micromoles Carboxyl per Gram Carboxymethyl reduced dextran T10 (40 g, prepared in Example 11) was dissolved in 850 ml water. To this was added a 0.2 μm filtered mixture of 29.9 g ferric chloride hexahydrate, 14.9 g ferrous chloride tetrahydrate, and 373 ml water. The mixture was cooled to 10° C., purged with nitrogen, 114 ml of 28% ammonium hydroxide solution was added with stirring, the mixture was heated to 90° C., maintained at 78° C. for 60 min, and then maintained at 78° C. while bubbling air through the mixture. The mixture was diluted with 1.5 liters of water, and filtered through a 0.2 μm filter. The product was purified by repeated ultrafiltration against a 100 kDa MWCO membrane, concentrated to 20 mg Fe/ml, and again filtered through a 0.2 μm filter.

Example 34

Preparation of USPIO Coated with Carboxymethyl Reduced Dextran T10 Having 280 Micromoles Carboxyl per Gram Carboxymethyl reduced dextran T10 (4 g, prepared in Example 12) was dissolved in 85 ml water. To this was added a 0.2 μm filtered mixture of 2.99 g ferric chloride hexahydrate, 1.49 g ferrous chloride tetrahydrate, and 37.3 ml water. The mixture was cooled to 10° C., and purged with nitrogen. To the mixture was added with stirring 11.4 g of 28% ammonium hydroxide solution, the mixture was heated to 90° C., maintained at 78° C. for 60 min, and then maintained at 78° C. while air was bubbled through the mixture. The mixture was diluted with 1.5 liters of water, and filtered through a 0.2 μm filter. The product was purified by repeated ultrafiltration against a 100 kDa MWCO membrane, followed by filtration through a 0.2 μm filter.

Example 35

Preparation of USPIO Coated with Carboxymethyl Reduced Dextran T10 Having 450 Micromoles Carboxyl per Gram Carboxymethyl reduced dextran T10 (4 g, prepared in Example 13) was dissolved in 85 ml water. To this was added a 0.2 μm filtered solution of 2.99 g ferric chloride hexahydrate, 1.49 g ferrous chloride tetrahydrate, and 37.3 ml water. The mixture was cooled to 10° C., and purged with nitrogen before adding 11.4 g of 28% ammonium hydroxide solution with stirring. The mixture was heated to 90° C., maintained at 78° C. for 60 min, and then maintained at 78° C. while air was bubbled through the mixture. The mixture was diluted with 1.5 liters of water, filtered through a 0.2 μm filter, and was purified by repeated ultrafiltration against a 100 kDa MWCO membrane followed by filtration through a 0.2 μm filter.

Example 36

Preparation of USPIO Coated with Carboxymethyl Reduced Dextran T10 Having 580 Micromoles Carboxyl per Gram Carboxymethyl reduced dextran T10 (40 g, prepared in Example 14) was dissolved in 85 ml water. To this was added a 0.2 μm filtered solution of 29.9 g ferric chloride hexahydrate, 14.9 g ferrous chloride tetrahydrate, and 373 ml water. The mixture was cooled to 10° C., purged with nitrogen, 11.4 g of 28% ammonium hydroxide solution with stirring. The mixture was heated to 90° C., maintained at 78° C. for 60 min, then maintained at 78° C. while bubbling air through the mixture. The mixture was diluted with 1.5 liters of water and filtered through a 0.2 μm filter, and was purified by repeated ultra-filtration against a 100 kDa MWCO membrane followed by filtration through a 0.2 μm filter.

The effect of degree of carboxymethylation of the CMRD coated USPIOs on colloid size was compared. Examples 31–36, Table 6. The MVD values of the resulting colloids were reasonably uniform between CMRD preparations con taining 110 to 1265 micromoles of carboxyl per gram of product.

TABLE 6

Particle sizes of USPIO colloids prepared with dextran T10 CMRDs having varying degrees of carboxymethylation.

| Example # | micromoles COOH/ g dextran | mean volume diameter, nm |
| --- | --- | --- |
| 32 | 110 | 12 |
| 33 | 130 | 15 |
| 34 | 280 | 18 |
| 35 | 450 | 16 |
| 36 | 580 | 20 |
| 31 | 1265 | 21 |

Example 37

Mixing of Carboxymethyl Reduced Dextran T10 Having 1,108 Micromoles Carboxyl per Gram with Ferric Chloride Solution As a step in particle synthesis, ferric chloride (0.3 g) was dissolved in 15 ml water and was filtered through a 0.2 μm pore size filter. Carboxymethyl reduced dextran (prepared in Example 6) was added, the mixture was shaken, and was cooled to 10° C. No precipitate was observed.

Example 38

Mixing of Carboxymethyl Reduced Dextran T10 Having 1,262 Micromoles Carboxyl per Gram with Ferric Chloride Solution Ferric chloride (0.3 g) was dissolved in 15 ml water and was filtered through a 0.2 μm pore size filter. Carboxymethyl reduced dextran (prepared in Example 7) was added, the mixture was shaken, and was cooled to 10° C. No precipitate was observed.

Example 39

Mixing of Carboxymethyl Reduced Dextran T10 Having 1,404 Micromoles Carboxyl per Gram with Ferric Chloride Solution Ferric chloride (0.3 g) was dissolved in 15 ml water and was filtered through a 0.2 μm pore size filter. Carboxymethyl reduced dextran (prepared in Example 8) was added, the mixture was shaken, and was cooled to 10° C. No precipitate was observed.

Example 40

Mixing of Carboxymethyl Reduced Dextran T10 Having 1,528 Micromoles Carboxyl per Gram with Ferric Chloride Solution Ferric chloride (0.3 g) was dissolved in 15 ml water and was filtered through a 0.2 μm pore size filter. Carboxymethyl reduced, dextran (prepared in Example 9) was added, the mixture was shaken, and was cooled to 5° C. An orange white precipitate was observed.

Example 41

Mixing of Carboxymethyl Reduced Dextran T10 Having 1,887 Micromoles Carboxyl per Gram with Ferric Chloride Ferric chloride hexahydrate (30.3 g) and ferrous chloride (14.8 g) were dissolved in 402.9 ml water and filtered through a 0.2 μm pore size filter. Carboxymethyl reduced dextran T10 (40.3 g in 1,033 ml, prepared in Example 15) was added, the mixture was shaken, and was cooled to 5° C. An orange white precipitate was observed.

The effect of varying the degree of carboxymethylation of CMRDs on the first step of the CMRD-USPIO synthesis, i.e., combining the aqueous mixtures of CMRD with the iron chloride solutions, was analyzed. The various CMRD preparations were mixed with iron salts at a fixed iron concentration, the CMRD preparations differing only in degree of carboxymethylation as described in Examples 37–41. From 1,108 to 1,404 micromoles carboxyl per gram dextran, the CMRD formed a homogeneous mixture in the presence of ferric chloride (Table 7).

TABLE 7

Precipitation of CMRDs having varying levels of carboxyl groups after addition of iron salts from mixtures of CMRD (25 mg/g solution) and ferric chloride (19 mg/g solution).

| Example # | micromoles COOH/g dextran | precipitate |
| --- | --- | --- |
| 37 | 1,108 | no |
| 38 | 1,262 | no |
| 31 | 1,265 | no |
| 39 | 1,404 | no |
| 40 | 1,528 | yes, at 5° C. |
| 41 | 1,887 | yes, at 25° C. |

At greater than 1,404 micromoles carboxyl per gram dextran, addition of ferric chloride under the conditions and concentrations of the USPIO synthesis to the CMRD solution produced an orange white precipitate. Even at higher temperatures, where many compounds can be soluble, the precipitates persisted. The data in Table 7 shows that there is an upper level in modification of CMRD that can be used in the preferred method of CMRD-USPIO synthesis.

Example 42

Synthesis of Iron Oxide Sols and Their Stabilization with Native and Reduced Dextrans and CMRD: Preparation of a Magnetic Sol To prepare a magnetic sol, 60 g of 28% of ammonium hydroxide at 25° C. was added to a solution having 30.0 g ferric chloride hexahydrate and 15.1 g ferrous chloride tetrahydrate in 321 g of water. After 5 minutes of mixing, sufficient concentrated HCl was added to obtain a pH of 1.6. The sol was ultrafiltered with a 100 kDa MWCO membrane filter to achieve a pH of 3.25, using water as diluent. The magnetic sol was passed through a filter of pore size 0.2 μm, then concentrated to 50 mg Fe/g, and stored at 5° C. The yield of iron was 55%, and the product was observed to have an MVD of 16 nm.

Example 43

Synthesis of Iron Oxide Sols and Their Stabilization with Native and Reduced Dextrans and CMRD: Preparation of a Non-magnetic Sol To a solution of 2.9 g of ferric chloride hexahydrate in 30 ml of water was added 10 ml of 10 M NaOH. The mixture was stirred for 5 min, diluted to 200 ml with water, and the product was collected by filtration. The residue was again mixed with water and filtered. The residue was added to 40 ml water and the pH was adjusted to 2.0. The product was observed to have an MVD of 10 nm.

Example 44

Synthesis of Iron Oxide Sols and Their Stabilization with Native and Reduced Dextrans and CMRD: Coating of a Magnetic Sol with Reduced Dextran T10

Reduced dextran T10 (60 mg; Example 3) was dissolved in 1.74 ml water and combined with 0.24 ml of magnetic sol (13 mg Fe) prepared according to Example 42. The mixture was incubated for 15 min, and the pH was adjusted to 7.4 with sodium hydroxide. The particle size (MVD) was determined to be 85 nm.

Example 45

Synthesis of Iron Oxide Sols and Their Stabilization with Native and Reduced Dextrans and CMRD: Coating of a Magnetic Sol with Native Dextran T10

Native dextran T10 (60.8 mg) was dissolved in 1.74 ml water, and combined with 0.24 ml of magnetic sol (13 mg Fe) prepared according to Example 42. The mixture was incubated for 15 min and the pH was adjusted to 7.4 with sodium hydroxide. The particle size (MVD) was determined to be 1,973 nm.

Example 46

Synthesis of Iron Oxide Sols and Their Stabilization with Native and Reduced Dextrans and CMRD: Coating of a Magnetic Sol with CMRD T10

75 mg of CMRD T10 (Example 5) dissolved in 1.34 ml water was added to 0.66 ml of magnetic sol (33 mg Fe) prepared according to Example 42. The mixture was incubated for 15 min at 37° C., and the pH was adjusted to 7.95 (plus or minus 0.4) with sodium hydroxide. The mixture was concentrated using a 300 kDa ultrafiltration filter. The product was observed to have an MVD of 41 nm.

Example 47

Synthesis of Iron Oxide Sols and Their Stabilization with Native and Reduced Dextrans and CMRD: Adjusting the pH of the Magnetic Sol to 7.4

A magnetic sol as prepared in Example 42 was adjusted to a pH of 7.4. A precipitate was observed.

Example 48

Synthesis of Iron Oxide Sols and Their Stabilization with Native and Reduced Dextrans and CMRD: Coating of a Non-magnetic Sol with CMRD T10

A non-magnetic sol prepared according to Example 43 (35 ml) was added dropwise to 35 ml of a 50 mg/g aqueous solution of CMRD T10 prepared according to Example 5. The pH was adjusted to 7.0 with 1 N NaOH, the solution was heated to boiling, cooled to room temperature, and was centrifuged at 6,000 rpm for 20 min. The supernatant was passed through a filter having a 0.2 μm pore size, and autoclaved at 121° C. for 30 min. The product was observed to have a MVD of 86 nm.

Examples 42–48 show that in the absence of a dextran, or in the presence of a native dextran, a gross iron precipitate forms. Only reduced dextran and CMRD yielded a magnetic sol as a stable colloid.

Example 49

Preparation of CMRD Coated Non-magnetic Iron Oxide Colloid Using Base Co-precipitation of Ferric Chloride and CMRD Carboxymethyl reduced dextran T10 (19.2 g) (Example 5) was dissolved in 300 g water, was filtered through a 0.2 μm filter, and an additional 160.8 g of water was added. This solution was added to 120 ml of 0.2 μm filtered aqueous 0.3 M ferric chloride hexahydrate. To this mixture was added 32 ml of aqueous 6N sodium hydroxide. The mixture was heated to 100° C. for 3 hours, cooled to room temperature, and ultrafiltered to a final volume of 50 ml. The product was observed to have an MVD of 30 nm. A portion of this material was placed in a bottle under nitrogen for 30 min at 121° C. The autoclaved product had an MVD of 69 nm.

Example 50

Effect of Autoclaving on Reduced and Native Dextran Colloids: Stability to Autoclaving of USPIOs Coated with Native Dextran and Reduced Dextran and CMRD Colloid preparations, each at a concentration of 20 mg Fe/g, were autoclaved for 30 min at 121° C. Following autoclaving, measurements were made of bound dextran which was calculated as the difference between total and free dextran, using a phenol/sulfuric acid assay. Free dextran was separated from the colloid by ultrafiltration. Table 8 shows that colloid preparations having USPIOs coated with a reduced dextran have greater stability than USPIOs coated with a native dextran. The reduced dextran coated USPIO maintained its small size following autoclaving, as the MVD of the post autoclaved material was increased only 1.3-fold compared to the MVD of the pre autoclaved material. In contrast, USPIO coated with native dextran increased in size 28-fold following autoclaving. The data show that following autoclaving, reduced dextran remains more tightly bound to the iron particle compared to native dextran.

A second type of increased stability achieved herein by use of reduced dextran to coat USPIO is the property of pH of the bulk solvent. The pH of USPIO coated with reduced dextran dropped 0.9 pH units following autoclaving, compared to a drop of 1.6 pH units for USPIO coated with native dextran.

Even greater stability to the autoclaving process was observed for particles coated with carboxymethyl reduced dextran compared to carboxymethyl native dextran. The data in Table 9 indicate that USPIO coated with carboxymethyl non-reduced native dextran showed a 10–50 fold increase in amount of particulate matter following autoclaving. In contrast, USPIO coated with carboxymethyl reduced dextran experienced no change in size or quantity of particulate matter upon autoclaving. Another indication of the stabilizing effect of the carboxymethyl reduced polysaccharides coating confer on the colloid suspension and bulk solvent was the stability of the solvent pH. The data in both Tables 8 and 9 show that the particles coated with reduced dextran had significantly improved pH stability upon autoclaving, compared to those coated with native dextran.

TABLE 8

Effect of autoclaving on pH, size, and bound polysaccharide of colloids coated with native and reduced dextran.

| | | pre autoclaved | | | post autoclaved[a] | | |
|---|---|---|---|---|---|---|---|
| Example | dextran coating | pH | bound dextran g/g | MVD nm | pH | bound dextran g/g | MVD nm |
| 29 | native T10 | 7.0 | 0.79 | 21 | 5.5 | 0.56 | 587 |
| 23 | reduced T10 | 7.4 | 1.26 | 18 | 6.7 | 0.96 | 23 |

[a]Samples were prepared at a concentration of 20 mg iron per ml and autoclaved for 30 minutes at 121° C.

TABLE 9

Effect of autoclaving on pH, size, and particulates of colloids coated with carboxymethylated reduced and carboxymethylated native non-reduced dextran.

| | | | | | | particulates[a] | | |
|---|---|---|---|---|---|---|---|---|
| Example | dextran | MVD | | pH | | >10 microns number/ml | | >25 microns number/ml |
| autoclaved | coating | pre | post | pre | post | pre | post | pre | post |
| 30 | CMD[b] | 19 | 18 | 7.5 | 6.8 | 35 | 433 | 5 | 240 |
| 31 | CMRD[c] | 25 | 18 | 8.0 | 7.9 | 4 | 7 | 1 | 5 |

[a]Particulates were determined by USP analysis.
[b]CMD, carboxymethyl dextran (native)
[c]CMRD, carboxymethyl reduced dextran
[d]Samples were prepared at a concentration of 20 mg iron per ml and autoclaved for 30 minutes at 121° C.

TABLE 10

| Material | Coating | Relaxivity Susceptibility | MW (kDa) | R1 | R2 | R2/R1 |
|---|---|---|---|---|---|---|
| Example 31 | reduced carboxymethyl dextran | 38,200 | 10 | 35.3 | 64.8 | 1.8 |
| Combidex® | Dextran-T10 | 28,000 | 9.6 | 21.7 | 60.3 | 2.8 |
| Gd-DTPA | | 172 | | 4.5 | 5.7 | 1.3 |

Example 51

Procedures for Determining Relaxation Properties of Various Contrast Agents Nuclear magnetic (NM) measurements (0.47T) were obtained in a Bruker Instruments pc120 table-top NM sample analyzer operating at 20 MHZ (Proton). Half a milliliter of each sample was placed in the 10 mm NM tubes for relativity measurements on the minispec. The placement of the sample in the sample chamber was optimized. The standards were run and their values recorded in the log.

Standard procedures were used for T1 and T2 determinations, and their values were recorded. T1 was measured using an inversion recovery technique. According to the IR technique, the sample is exposed to a 180° pulse and then a 90° pulse to put the magnetization in the plane of detection. After sampling; the time between the 180 and 90-degree pulses is changed, and sampled again. This is done for several durations. The resulting signals are governed by the equation $[M_\infty - M(t)]/M_\infty = (1 - \cos\Theta)\exp(-t/T1)$. When a 3 parameter fit to data is performed, $M_\infty$, $\Theta$, and T1 are calculated.

T2 was measured using the CPMG technique, where a linear train of 180° pulses of variable length is provided to the sample. The amplitude of every second echo is measured. A fit is performed on the accumulated data using a two parameter ($M_0$ and T2) fit. Where $M(t) = M_0 \exp(-t/T2)$, a plot of $\ln(M(t))$ versus t is linear with a slope of $-1/T2$. The inverse of the T1 and T2 was graphed with respect to the iron concentration of the sample. From the slope of best fit line the relaxivity was determined.

Example 52

Toxicity Studies in Rats. Toxicity of Reduced Dextran, Non-reduced Dextran, and CMRD Coated Colloids Administered in Vast Excess to Rats An anaphylactic shock type of reaction to dextran can be exhibited by rats and by a small but significant fraction of the human population (Squire, J. R. et al., "Dextran, Its Properties and Use in Medicine," Charles C. Thomas, Springfield, Ill., 1955). The reaction resembles anaphylactic shock but does not require prior sensitization, and is characterized in rats by the rapid development of prostration, diffuse peripheral vasodilation, and edema of paws, snout and tongue (Voorhees, A. B. et al., Proc. Soc. Exp. Biol. Med. 1951, 76:254). When accompanied by barbiturate anesthesia, it produces marked hypotension and cyanosis (Hanna, C. H. et al., Am. J. Physiol. 1957, 191:615).

A procedure to measure the extent of rat paw edema response was employed to determine if the presence of reduced dextrans or their derivatives, rather than non-reduced native dextrans, in the coating of the iron oxide colloids could decrease or eliminate potential human adverse reactions upon intravenous injection. Rat paw edema was measured as the volume of the paw prior to and subsequent to injection of test material, using a plethysmometer, which is a differential volume measuring device. The dose of test material was injected, and a second reading was taken after a designated interval, and the per cent change in paw volume was calculated. The dose administered in these studies was 100 mg Fe/kg body weight, a dose much greater than that used as an imaging agent in rats, pigs, and humans (see Examples 53–56).

The results observed following administration of iron oxides coated with each of reduced and non-reduced T10 dextrans are shown in Table 11. A marked decrease in the edematous anaphylactic response was observed in those rats which were administered a USPIO preparation having the reduced dextran or reduced dextran derivatives as a coating, compared to those rats administered a USPIO preparation having a native non-reduced dextran coating.

TABLE 11

Effect of native and reduced polysaccharide coated particles on rat edema.

| Example | coating and particle | % edema |
|---|---|---|
| 29 | native dextran coated USPIO | >50 |
| 23 | reduced dextran coated USPIO | 13 |
| 30 | carboxymethyl native dextran coated USPIO | 39 |
| 48 | carboxymethyl reduced dextran non-magnetic colloid | 12 |
| 31 | carboxymethyl reduced dextran coated USPIO | 0 |

The effect of the CMRD-USPIO preparations having increasing levels of carboxymethyl substitution on the extent of anaphylactic response, measured as percent edema, is shown in Table 12. The data show that a threshold level of substitution was necessary to reduce the edematous response, and that once this threshold of substitution was achieved, the decrease in response of the rats to dextran was a surprising elimination of the edematous response. That is, no edema was observed at 1,265 micromoles of carboxyl per gram.

TABLE 12

Extent of rat paw edema as a function of amount of carboxymethylation of dextran coating of USPIOs.

| Example | micromol COOH per g dextran | % edema |
|---|---|---|
| 32 | 110 | 24 |
| 33 | 130 | 54 |
| 34 | 280 | 81 |
| 35 | 450 | 37 |
| 36 | 580 | 105 |
| 31 | 1,265 | 0 |

Example 53

Toxicity Studies in Rats of Reduced and Non-reduced Dextrans

The procedure used in Example 52 was used to determine if the coating alone, that is, reduced dextrans or their derivatives rather than non-reduced native dextrans, could eliminate potential human adverse reactions upon intravenous injection. Rat paw edema was measured as the volume of the paw prior and subsequent to injection, as in Example 52. The dose administered in these studies was, as above, 100 mg test substance/kg body weight.

The results observed following administration of reduced and non-reduced T10 dextrans were similar for each material (Table 13). Reduced dextran T10 elicited the same extent of edema as native dextran T10. Elimination or decrease in edema could not be attributed merely to reduction of the dextran.

TABLE 13

Effect of native and reduced 10 kDa polysaccharides on rat edema showing mere reduction has no significant effect

| Example | test dextran | % edema |
|---|---|---|
| Dextran T-10 (commercial[a]) | native T10 | 61 |
| 3 | reduced T10 | 67 |

[a]Obtained from Pharmacia-Upjohn (Piscataway, NJ)

Table 14 shows the effect of increased levels of carboxymethyl substitution of reduced dextran on the extent of anaphylactoid response, measured as percent edema. The data show that above a threshold level of carboxymethyl substitution, edema was decreased or eliminated. For dextrans above this threshold level of substitution, the decrease in the toxic response of the rats to dextran was a surprising elimination of response, that is, no edema was observed.

TABLE 14

Relationship between rat paw edema and degree of carboxymethylation of dextran T10 preparations.

| Example | test substance | micromol COOH/ g per dextran | % edema |
|---|---|---|---|
| 10 | carboxymethyl reduced | 110 | 65 |
| 12 | carboxymethyl reduced | 280 | 60 |
| 13 | carboxymethyl reduced | 450 | 56 |
| 5 | carboxymethyl reduced | 1,265 | 6 |
| 15 | carboxymethyl reduced | 1,887 | 1 |
| 16 | carboxymethyl native | 1,220 | 0 |

Example 54

Pharmacokinetics of CMRD Coated USPIO in the Rat: Blood Clearance

Three male CD® rats (Charles River Laboratories, Wilmington, Mass.; weight range 272 to 290 g) were anaesthetized intraperitoneally with a long lasting anesthetic, Inactin (100 mg per kg body weight). The femoral artery and vein were exposed by a small incision at the hip-femur joint, and the artery was cannulated with PE50 tubing connected to a 1 ml syringe filled with heparinized saline (10 units per ml). To serve as a baseline, 0.25 ml of arterial blood was collected at time zero, and CMRD coated USPIO (Example 31) was injected into the femoral artery. Blood samples of 0.25 ml were collected at the times indicated in FIGS. 4 and 5.

T2 magnetic relaxation times were measured in each sample, and the relaxivity (1/T2) was calculated. First-order reaction kinetics were used to determine the half-life of the sample in the blood ($t_{1/2}$). The equation used to fit the data was:

$$1/T_2 - 1/T_{baseline} = Ae^{-kt}$$

where $1/T_2$ is the relaxivity of the blood at time t post-injection; $1/T_{baseline}$ is the baseline relaxivity, and $Ae^{-kt}$ represents the first-order decay of the test material from the blood. Taking the natural log of each side of this equation yields:

$$\ln (1/T2-1/T_{baseline}) = -kt + \ln A_0$$

According to this second equation, a graph of ln (1/T2−1/T$_{baseline}$) versus time, t, should give a straight line with slope −k (the first order rate constant) and intercept lnA$_0$ (which equals ln (1/T2−1/T$_{baseline}$ at time zero) if the rate of removal of the USPIO from blood follows first order kinetics. FIG. 5 shows that a straight line was obtained. The half-life ($t_{1/2}$), which is the time that the amount of CMRD coated USPIO decreased to one half its amount of concentration in the blood, was determined to be 67 min, with a range of 61 to 75 min at a confidence level of 95%.

Example 55

Magnetic Resonance Imaging Using CMRD Coated USPIO in the Rat

Figure 6B:
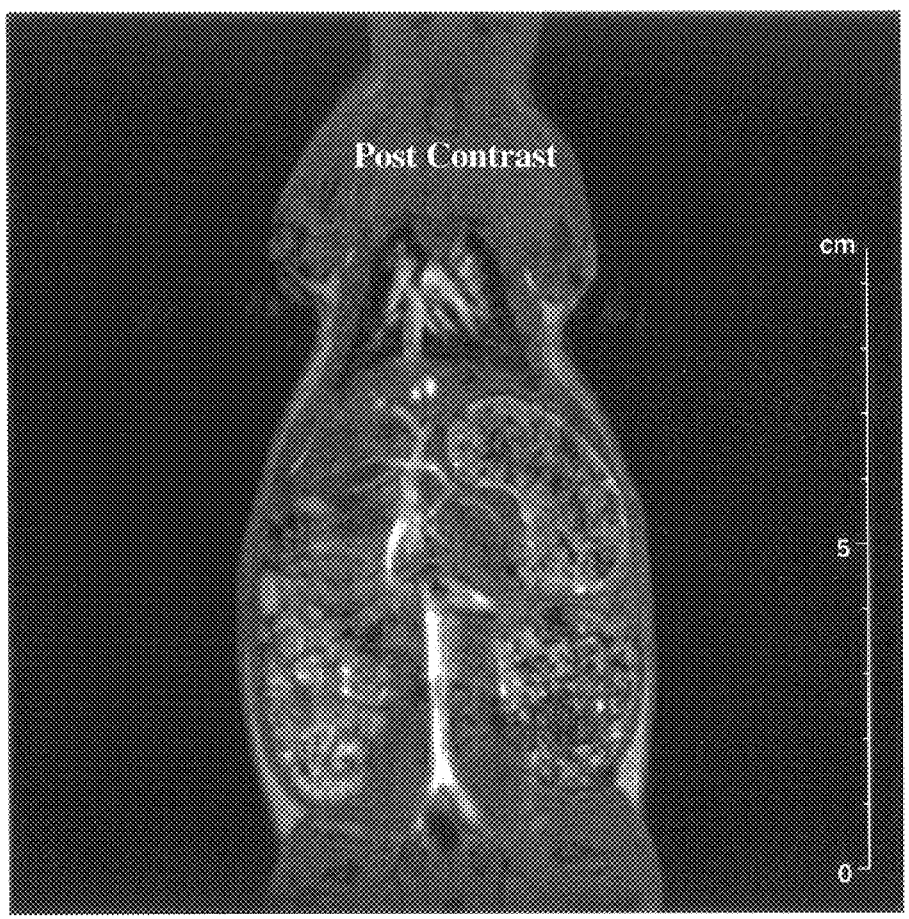

An MRI scan of a rat taken shortly after administration of 5 mg of CMRD coated USPIO (Example 31) per kg body weight is shown in FIG. 6B. The heart, aorta, and coronary artery were found to be readily imaged using this agent. An image of the rat taken pre-administration of the agent (FIG. 6A) is included to illustrate the substantial increase in contrast effected by administration of the test substance.

Example 56

MRI of CMRD Coated USPIO in the Pig

Figure 7A:
FIG. 7 shows MRI images of a pig, pre-administration (A) and post-administration (B) of contrast agent, anterior portion at top. CMRD coated USPIO (Example 31; 4 mg of iron per kg body weight) was administered into the femoral vein prior to taking the post administration contrast image. The figure illustrates enhanced visualization of the heart and surrounding arteries and veins caused by administration of CMRD coated USPIO. Imaging was performed using a Siemans 1.5T Magnatom Vision magnetic resonance imager.
Figure 7B:
Figure 8A:
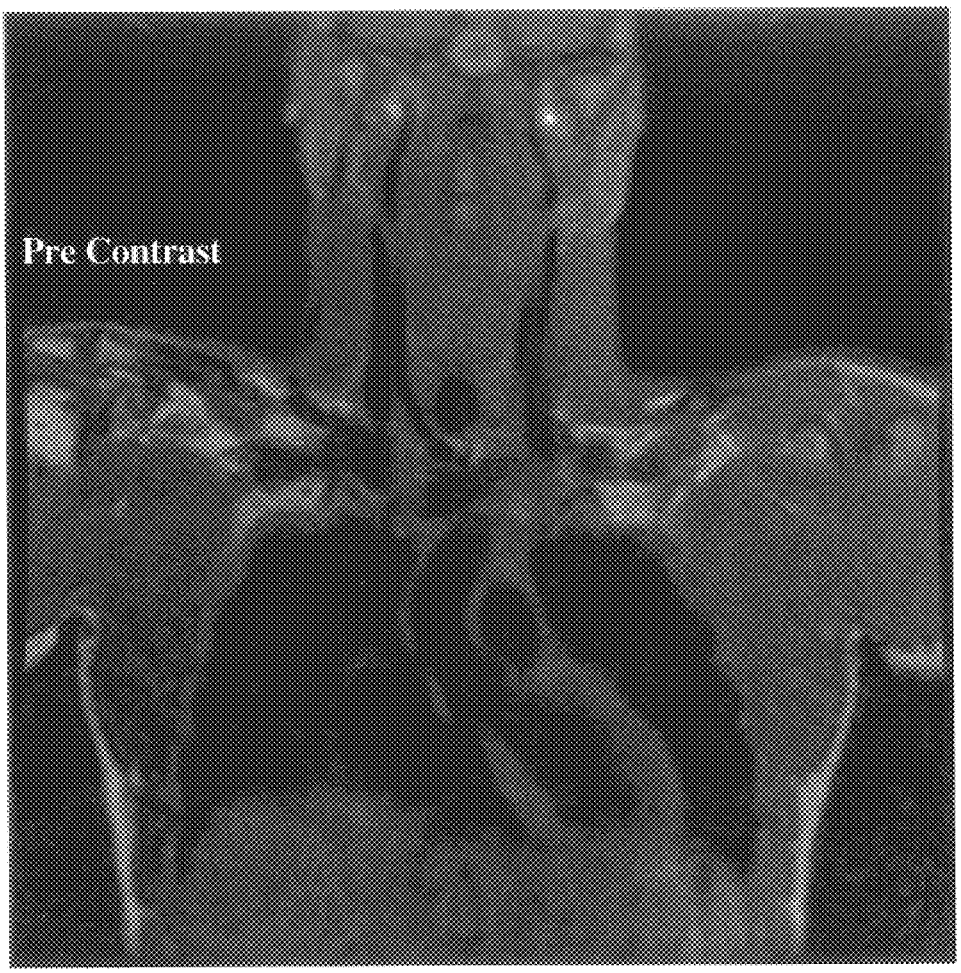
FIG. 8 shows MRI images of the anterior portion of a normal human subject, pre-administration (A) and post-administration (B) of contrast imaging agent. CMRD coated USPIO (4 mg of iron per kg body weight) was administered as a bolus into a vein in the arm prior to taking the post contrast image. Imaging was performed 15 to 30 minutes after administration of contrast agent. The image illustrates enhanced visualization of the heart and surrounding arteries and veins.

FIG. 7 illustrates enhanced MRI visualization of the heart and surrounding arteries, as well as the lungs and kidneys of the pig. Four doses of 0.4, 0.8, 1.6, and 2.2 mg of iron/kg body weight of sample (Example 31) were each administered to the pig in sequential order. Each dose was followed by administration of 20 ml of physiological saline, and an MRI image was obtained after each dose. The image shown in FIG. 7B is representative of images obtained after each administration. A preimage of the pig (FIG. 7A) is included to illustrate the substantial increase in contrast effected by the agent.

A problem associated with low molecular weight gadolinium based contrast agents is that they leak from the vascular space into the interstitial space and create a hazy background. This hazy background interferes with effective use of second or third injections of a contrast agent administered during a single examination. Such extravascular leakage might not be expected with carboxymethyl reduced dextran-coated USPIOs due to the relatively large size of the particle, compared to the size of the particles of a gadolinium contrast agent.

This expectation was confirmed by imaging of rats (Example 55) and in the data obtained by imaging of the pig (FIG. 7B). No background haze was observed following use of the CMRD USPIO compositions of the present invention. This observation enabled performance of additional vascular imaging tests, after sequential administration of additional doses. Upon intravenous administration, the CMRD coated USPIO, which is an embodiment of the invention, moved as a bolus rapidly into the arteries, organs, and veins, and achieved a uniform distribution in the blood after 20 minutes. Upon administration of a second bolus of the agent, additional good images were obtained. A third injection and a fourth injection were administered with similar results i.e., good images were obtained. Thus, the process of bolus injection and first pass application of the CMRD coated USPIO was demonstrated. Further, application of a multiple injection protocol within a reasonably short period of time after the first administration, the entire protocol being accomplished in a time period equivalent to a visit by a human subject to an imaging facility, was also demonstrated.

The principal advantages of capability of multiple bolus injections within a single examination are the opportunities to correct a deficiency in imaging that might arise after an injection, and to image multiple parts of the body during a single examination. In this manner, additional sites within the body of a subject can be imaged within a short period of time after scanning and analysis of earlier images from an earlier pass, and subsequent injections of contrast agent can be used to obtain different views, or to extend the view in one or more physical dimensions. For example, detailed analysis of the location and size of a blood clot in a limb such as a leg, can be performed using a series of views taken in the each of a first, second, and subsequent passes.

The capability for achieving additional multiple passes of administration of a composition of the invention and obtaining additional rounds of MRI data, beyond a first dose, present strong advantages of the compositions that are embodiments of the present invention. MRI analyses have in the past been limited by the physical length of the anatomical feature in need of imaging, and by the numbers of structures that can be imaged using a single detection instrument unit in a given time period.

The results obtained in pigs were observed also in human subjects (Examples 57 and 58).

Example 57

Intravenous Injection of CMRD Coated USPIO into Normal Human Subjects

The trial design employed thirty-five human subjects each administered one dose of CMRD T10 coated USPIO prepared according to Example 31(i.v.; 1–4 mg of iron/kg body weight). The objectives of Examples 57 and 58 were to examine subjects for any potential side effect of the treatment, to obtain data on the composition as an MRI contrast agent, and to determine the half-life of the composition in blood.

No adverse reactions attributable to administration of the composition were observed among the treated subjects at any dose, including the highest doses (4 mg/kg). For comparison, in clinical trials of Feridex I.V.®, approximately 2–3% of treated patients reported back pain, even though Feridex I.V.® and other comparable imaging products are administered in much smaller doses (e.g., 0.56 mg of iron/kg body weight) in order to minimize adverse events and obtain useful contrast. These data indicate that an effective dose of the CMRD coated USPIO particles of the invention is safer than an effective dose of a previously approved imaging agent, Feridex I.V.®

Example 58

Rapid Imaging Kinetics and Bio-distribution in Human Subjects

Figure 8B:
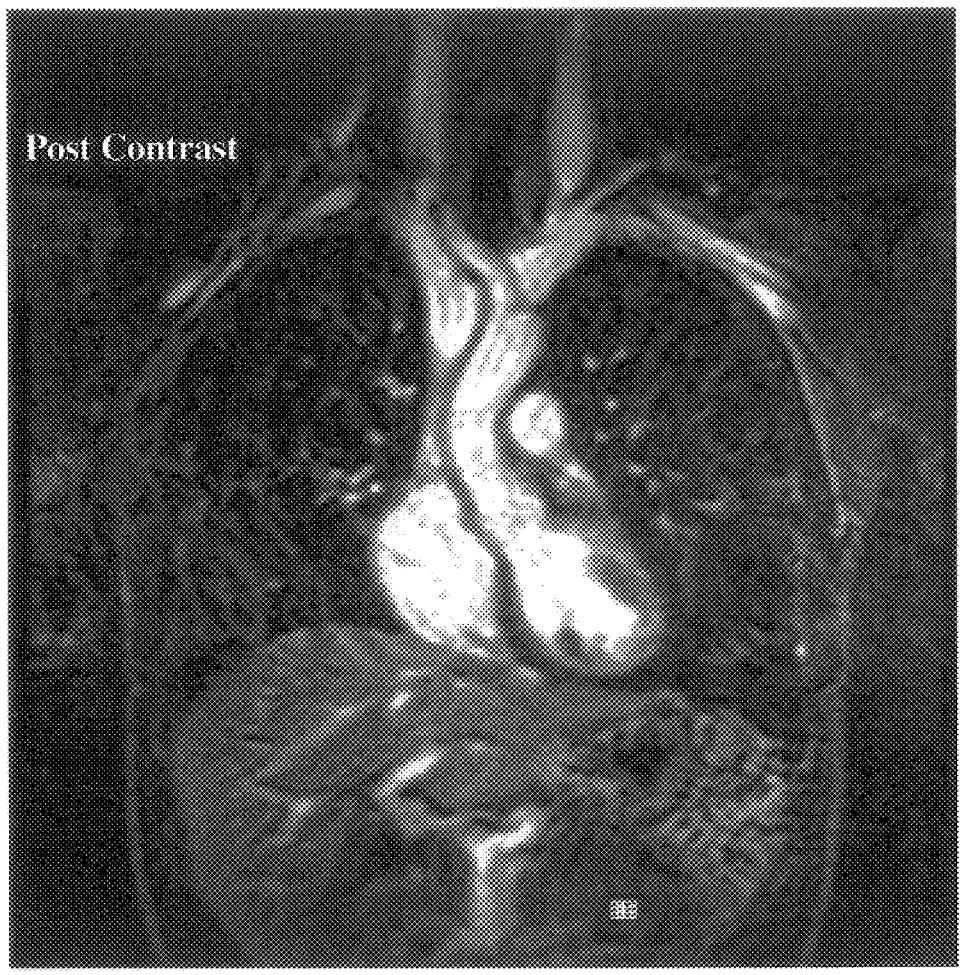
Figure 9A:
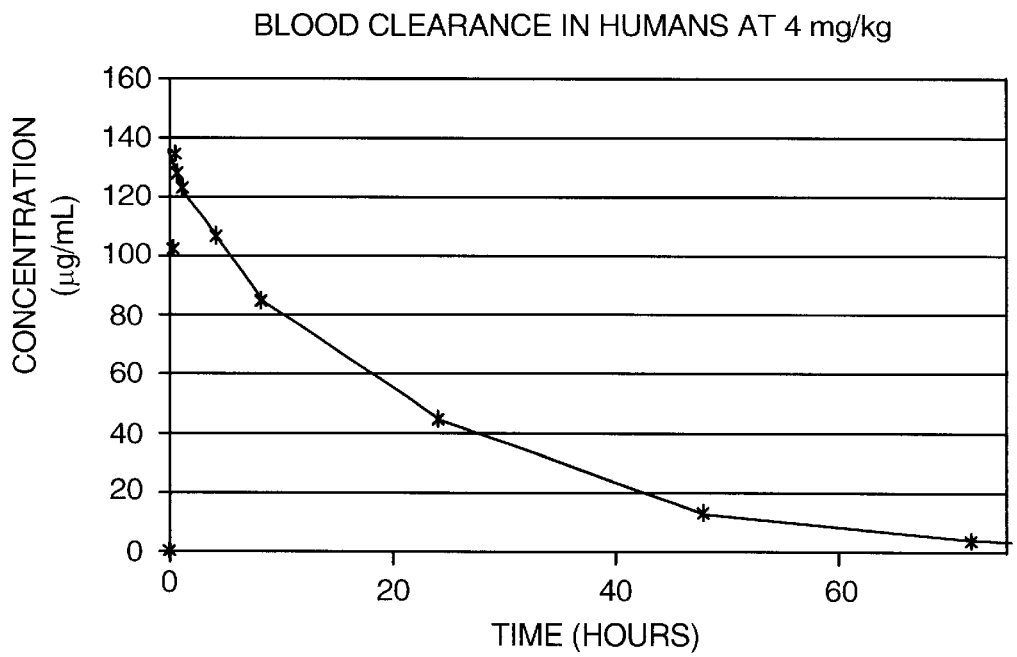
FIG. 9 shows the blood clearance kinetics in humans of imaging agent. CMRD coated USPIO (4 mg of iron per kg body weight), was administered as a bolus into a vein in the arm prior to taking blood samples. Samples were analyzed for 1/T2 relaxation to determine the blood concentration of the CMRD coated USPIO. The graph shows CMRD coated USPIO concentration (ordinate) as a function of time (abscissa).
Figure 9B:
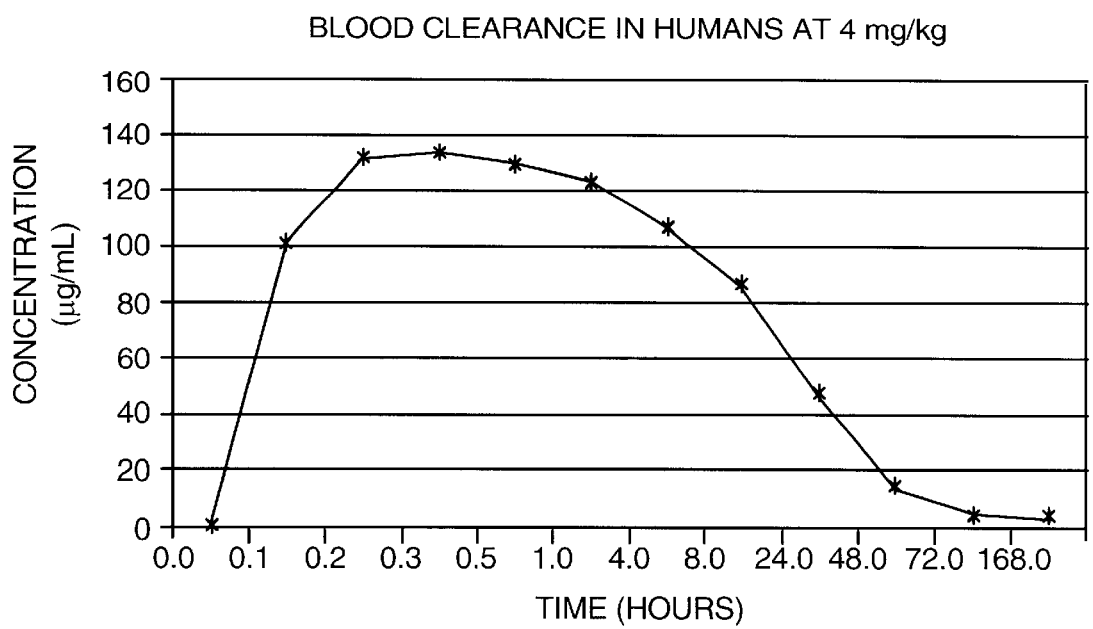

An initial intravenous bolus injection into human subjects of CMRD coated USPIO, prepared as in Example 31 yielded a bright MRI of the arterial portion of the circulatory system within 12 seconds post-administration (FIG. 8B). Following a further 15 seconds, MRI exposures yielded bright images of organs and veins. Equilibration of the agent throughout the vascular system was achieved within 20 minutes.

The organs capable of being imaged in the early phase following administration of the CMRD coated USPIO of the present invention included the heart, arteries and veins. Further, in addition to the larger elements of the circulatory system, the arterioles and venules of the extremities (fingers, toes) could be observed. This level of resolution allows applications to diagnosis of problems in circulation within the extremities, including the detection and localization of an area of phlebitis. Other organs that were readily imaged include the brain, kidneys, liver, spleen, and bone marrow. Lymph nodes could be imaged up to several hours after administration of an effective dose. The half-life of the agent in the blood was approximately observed to be 10–14 hours (see Table 15 and FIG. 9).

The particles ultimately were removed from circulation by being taken up by the reticuloendothelial system. During the presence of the composition at the early phase in the vascular system, and also in the late or post vascular phase in the reticuloendothelial system (RES), this composition was not observed to enter into interstitial spaces between cells. Thus, a hazy background, found to appear with usage of other compositions, for example, gadolinium based MR contract agents such as Magnevist® and DOTOREM®, is avoided during use of the CMRD-USPIO compositions, as synthesized by the methods of the Examples herein.

TABLE 15

Mean half-life of CMRD-USPIO T10 in human subjects as a function of dose.

| Dose mg iron/kg | half-life, hours | standard deviation | # subjects |
|---|---|---|---|
| 1 | 9.7 | 1.1 | 8 |
| 2 | 10.3 | 1.4 | 8 |
| 4 | 14.4 | 2.2 | 17 |

What is claimed is:

1. A method of providing an iron oxide complex for administration to a mammalian subject, the method consisting of:
   producing a carboxyalkylated reduced polysaccharide iron oxide complex; and
   sterilizing the complex by autoclaving.

2. A method according to claim 1, wherein the reduced polysaccharide is a reduced polymer of glucose.

3. A method according to claim 2, wherein the reduced polymer of glucose is a reduced dextran.

4. A method according to claim 1, wherein the reduced polysaccharide is produced by reacting a polysaccharide with a reagent selected from the group consisting of: a borohydride salt, and hydrogen in the presence of an hydrogenation catalyst.

5. A method according to claim 1, wherein producing the complex includes carboxyalkylating a reduced polysaccharide by carboxymethylation.

6. A method according to claim 5, wherein the reduced polysaccharide is a reduced dextran.

7. A method according to claim 6, wherein the administration to a mammalian subject is administration to a human.

8. A method according to claim 1, wherein the carboxyalkylated, reduced polysaccharide isolated as a sodium salt does not contain an infrared absorption peak in the region of about 1650 cm$^{-1}$ to about 1800 cm$^{-1}$.

9. A method according to claim 1, wherein producing the carboxyalkylated reduced polysaccharide is achieved at a temperature of less than about 50° C.

10. A method according to claim 11, wherein producing the carboxyalkylated reduced polysaccharide is achieved at a temperature of less than about 40° C.

11. A method according to claim 1, wherein the iron oxide is superparamagnetic.

12. A reduced polysaccharide iron oxide complex produced according to the method of claim 1, wherein the produced complex is stable at a temperature of at least 100° C.

13. A reduced carboxyalkylated polysaccharide iron oxide complex wherein the produced complex is stable at a temperature of about 121° C.

14. A reduced polysaccharide iron oxide complex according to claim 13, wherein the produced complex is stable at a temperature of at least about 121° C. for a period of time effective to sterilize the complex.

15. A reduced polysaccharide iron oxide complex according to claim 14, wherein the carboxyalkylated reduced polysaccharide is selected from the group consisting of a carboxymethyl, carboxyethyl and carboxypropyl reduced polysaccharide.

16. A reduced polysaccharide iron oxide complex according to claim 15, wherein the reduced polysaccharide is a reduced dextran.

17. A reduced polysaccharide iron complex according to claim 15, wherein the carboxyalkylated reduced dextran is a carboxymethyl reduced dextran.

18. A reduced polysaccharide iron oxide complex according to claim 16, wherein the carboxyalkylated reduced dextran comprises at least about 750 micromole of carboxyl groups per gram of polysaccharide.

19. A reduced polysaccharide iron oxide complex according to claim 18, wherein the carboxyalkylated reduced dextran comprises at least about 900 micromole of carboxyl groups per gram of polysaccharide.

20. A reduced polysaccharide iron oxide complex according to claim 19, wherein the carboxyalkylated reduced dextran comprises at least about 1100 micromole of carboxyl groups per gram of polysaccharide.

21. A reduced polysaccharide iron oxide complex according to claim 20, wherein the carboxyalkylated reduced dextran comprises less than about 1500 micromole of carboxyl groups per gram of polysaccharide wherein said complex does not form substantial particulates.

22. A method of providing a contrast agent for in vivo MRI of a subject according to claim 1, consisting of the steps of:
   formulating a composition which is a carboxymethylated reduced ultrasmall superparamagnetic iron oxide complex; and
   terminally sterilizing the composition by autoclaving.

23. A method of providing a hematinic agent for treating a subject deficient in iron, consisting of the steps of:
   formulating a composition which is a carboxymethylated reduced ultrasmall iron oxide complex; and
   terminally sterilizing the composition by autoclaving.

24. A method according to claim 22 or 23, having the further step of providing the autoclaved composition in a unit dosage.

25. A reduced carboxyalkylated polysaccharide iron oxide complex which is stable at a temperature of about 121° C., wherein a sodium salt of the complex does not contain an infrared absorption peak in the region of about 1650 cm$^{-1}$ to about 1800 cm$^{-1}$.

26. A reduced carboxyalkylated polysaccharide iron oxide complex according to claim 25, wherein the polysaccharide is carboxymethylated.

* * * * *

UNITED STATES PATENT AND TRADEMARK OFFICE
CERTIFICATE OF CORRECTION

PATENT NO. : 6,599,498 B1
DATED : July 29, 2003
INVENTOR(S) : Ernest V. Groman et al.

It is certified that error appears in the above-identified patent and that said Letters Patent is hereby corrected as shown below:

Title page, Item [54] and Column 1, line 3,
Replace "CARBOHDRATE" with -- CARBOHYDRATE --

Column 7,
Scheme 1, lines 14-20, replace compound 2 with the following:

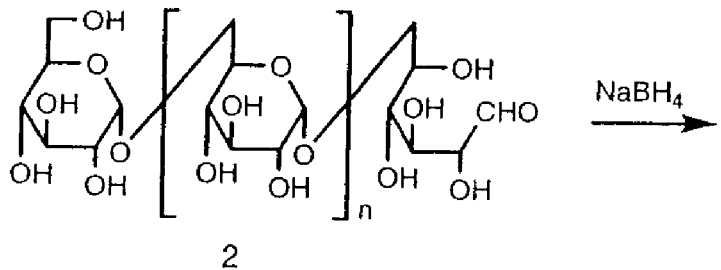

Column 13,
Line 21, replace "edemia" with -- edema --.

Signed and Sealed this

Second Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,599,498 B1
APPLICATION NO. : 09/521264
DATED : July 29, 2003
INVENTOR(S) : Ernest V. Groman et al.

It is certified that error appears in the above-identified patent and that said Letters Patent is hereby corrected as shown below:

In Col. 13, line 17
replace "symtoms"
with --symptoms--.

In Col. 13, line 22
replace "edemia"
with --edema--.

In Col. 37, claim 10, line 65
replace "claim 11"
with --claim 9--.

In Col. 38, claim 13, line 8
replace "produced"
with --reduced--.

In Col. 38, claim 14, line 11
replace "produced"
with --reduced--.

In Col. 38, claim 22, line 46
insert --polysaccharide--
immediately after "reduced".

In Col. 38, claim 23, line 50
insert --according to claim 1,--
immediately after "iron,".

UNITED STATES PATENT AND TRADEMARK OFFICE
CERTIFICATE OF CORRECTION

PATENT NO.         : 6,599,498 B1
APPLICATION NO.    : 09/521264
DATED              : July 29, 2003
INVENTOR(S)        : Ernest V. Groman et al.

It is certified that error appears in the above-identified patent and that said Letters Patent is hereby corrected as shown below:

In Col. 38, claim 23, line 52
insert --polysaccharide--
immediately after "reduced".

Signed and Sealed this

Twenty-seventh Day of January, 2009

JOHN DOLL
*Acting Director of the United States Patent and Trademark Office*